United States Patent [19]

Lefrancier et al.

[11] Patent Number: 4,461,761
[45] Date of Patent: Jul. 24, 1984

[54] OLIGOMERS OF COMPOUNDS OF THE MURAMYL-PEPTIDE TYPE AND MEDICAMENTS CONTAINING THEM

[75] Inventors: Pierre Lefrancier, Bures sur Yvette; Monique Parant, Paris; Francoise Audibert, Neuilly sur Seine; Edgar Sache, Bures sur Yvette; Louis Chedid; Jean Choay, both of Paris; Edgar Lederer, Sceaux, all of France

[73] Assignee: Agence Nationale de Valorisation de la Recherche (ANVAR), NeuillysurSeine, France

[21] Appl. No.: 410,727

[22] Filed: Aug. 23, 1982

Related U.S. Application Data

[63] Continuation of Ser. No. 268,500, May 29, 1981, abandoned, which is a continuation of Ser. No. 44,672, Jun. 1, 1979, abandoned.

[30] Foreign Application Priority Data

Jun. 5, 1978 [FR] France ................. 78 16792

[51] Int. Cl.³ .................... A61K 37/00; C07C 103/52
[52] U.S. Cl. ................... 424/177; 260/112.5 R
[58] Field of Search ............... 260/112.5 R; 424/177

[56] References Cited

U.S. PATENT DOCUMENTS

| | | | |
|---|---|---|---|
| 3,855,197 | 12/1974 | Hirsch et al. | 424/177 |
| 4,036,953 | 7/1977 | Adam et al. | 424/177 |
| 4,082,735 | 4/1978 | Jones et al. | 424/177 |
| 4,082,736 | 4/1978 | Jones et al. | 424/177 |
| 4,153,684 | 5/1979 | Audibert et al. | 424/177 |
| 4,314,999 | 2/1982 | Debarbieri | 260/112.5 R |
| 4,370,265 | 1/1983 | Adam et al. | 260/112.5 R |

FOREIGN PATENT DOCUMENTS

| | | | |
|---|---|---|---|
| 852349 | 2/1976 | Belgium | 424/177 |
| 852348 | 2/1976 | Belgium | 424/177 |
| 834753 | 2/1976 | Belgium | 424/177 |
| 834754 | 2/1976 | Belgium | 424/177 |
| 849214 | 9/1977 | Belgium | 424/177 |
| 3833 | 9/1979 | European Pat. Off. | 424/177 |
| 2046020 | 9/1975 | Japan | 424/177 |
| 2015534 | 9/1979 | United Kingdom | 424/177 |

OTHER PUBLICATIONS

F. Ellorz et al., Biochem. & Biophys. Res. Commun., 59, (1974), 1317–1325.
Adam et al., Biochem. & Biophys. Res. Commun., 72, (1976), 339–346.
Parant et al., Biol. Abstr. 67, 54289.
Parant et al., Chem. Abstr. 90, 20599p.
Chem. Abstr., vol. 93 (1980) 95663a, 186796n.

Primary Examiner—Delbert R. Phillips
Attorney, Agent, or Firm—Weiser & Stapler

[57] ABSTRACT

The novel products are water-soluble oligomers, free of N-acetyl-glucosamine units, and of which the monomer elements include a group derived from muramic acid on which is fixed a chain of the peptide type including at least two aminoacyl residues, the first being selected from among: L-alanyl, L-arginyl, L-asparagyl, L-histidyl, L-hydroxyprolyl, L-isoleucyl, L-leucyl, L-methionyl, L-phenylalanyl, L-prolyl, L-seryl, L-threonyl, L-tryptophanyl, L-valyl, and the second aminoacyl is D-glutamyl or D-isoglutaminyl. They are useful for their immunoregulator properties and for the preparation of pharmaceutical compositions.

7 Claims, No Drawings

OLIGOMERS OF COMPOUNDS OF THE MURAMYL-PEPTIDE TYPE AND MEDICAMENTS CONTAINING THEM

This is a continuation of application Ser. No. 268,500, filed May 29, 1981, now abandoned, which in turn is a continuation of Ser. No. 044,672, filed June 1, 1979, now abandoned.

The invention relates to novel products endowed with biological and pharmacological properties of great value, which can be exploited either for the constitution of standardized laboratory reactants for the comparative study of similar biological properties of other compounds, or for the constitution of new medicaments for human or veterinary use.

More particularly, the invention relates, among these compounds, to those which possess immunoregulator properties, notably non-specific immunological adjuvants, these compounds being suitable, among other activities, for reinforcing the immunoprotector activity of natural or synthetic immunogenic agents of all types, whether it relates to immunogenic agents which are weak by nature, strong immunogenic agents, but used at very low doses, or agents whose immunogenic effect, initially strong, has been considerably reduced due to the fact of the purifications or modifications to which these agents have given rise, to reduce their toxicity or the side-effects which accompany their in vivo administration.

The invention also relates therefore to the applications to which the compounds, according to the present application, are capable of giving rise, as well as the particular compositions containing such compounds, more particularly suitable for the practising of these applications.

It relates therefore to biological reactants, for example standard immunological adjuvants, which can be constituted by means of the compounds according to the invention, notably in order to study the possible adjuvant properties of substances to be investigated by comparison with such standard adjuvants or, on the contrary, as agent capable of countering certain effects linked with the administration of these immunosuppressor substances.

The invention relates more particularly also to the application of the compounds concerned to the amplification of the immunogenic effect of active principles of vaccines administered to a host, animal or human, notably in the case where these vaccinating principles belong to categories of immunogenic agents recalled above. Consequently, the invention relates equally also to pharmaceutical compositons whose active principle is constituted by at least one of the compounds defined below, in association with a suitable pharmaceutical vehicle for the mode of administration required or useable having regard to the nature of the vaccinating principle used.

The invention relates more particularly to novel products capable of modifying the immune responses in warm-blooded creatures. More specifically again, it relates to novel products capable of stimulating the immune responses which bring into play at least one and preferably all of the mechanisms constituting the humoral immune response support (opsonins, antibodies), or the cell mediated immune response. These mechanisms may be specific (their intervention depending on prior vaccination by a given antigen mixture, and more especially derived from pathogenic agents), or non-specific (such as are induced by agents such as BCG, corynebacteria or endotoxins).

It is known that organisms of warm-blooded creatures comprise several types of cells constituting what could be called several lines of defense with respect to the various aggressions to which these organisms may be subject.

The first line of defense brings into play, as is well-known, the leucocytes and macrophages in the blood stream, capable, when they encounter a foreign agent such as an antigen, of phagocyting it and often of destroying it. This phagocytosis can be facilitated notably by non-specific constituents of the serum (opsonins), even by external interventions leading to activation of the macrophages.

A second line of defense of the organism brings into play mechanisms triggered by antigenic constitutents of the foreign agent. These immune mechanisms bring into play cellular differentiations in at least one of two of the following principal directions.

A first type of immune mechanism brings into action specialized cells (B lymphocytes) which are precursors of the cells which secrete immunoglobulins or antibodies. These immunoglobulins or antibodies play an important role in the battle against infection caused by bacteria or other micro-organisms which replicate in the humoral fluids, or again to neutralize toxins or the like. With this type of action, specific to the antigen concerned, is added an indirect action by circulating mediators, which is manifested by activation of the cells responsible for phagocytosis, thus reinforcing the non-specific defenses of the organism.

The second type of immune mechanism brings into play specifically sensitized cells belonging to the lymphocyte line (T cells), which interact on the previously indicated B cells, or on the macrophages leading to activation of the latter or of other non-specific cells.

In the face of these various mechanisms presented diagrammatically below, it is possible to distinguish two types of infection according to the manner in which they develop and the mechanisms which are obliged to combat them. Thus, for certain infections, a simple phagocytosis, facilitated possibly by specific humoral or non-humoral factors, permits the destruction of the infectious agents. For other types of infections, phagocytosis is not sufficient.

The phagocyted infectious agent is not destroyed and even continues to act within the phagocyting cell, resulting on the contrary in the destruction of the latter. In this case, to prevent intracellular growth of the infectious agents, it is necessary to "activate" the phagocyting cells according to the above-indicated processes.

When it is desired to study the anti-infectious properties of novel products, the Klebsiella, as infecting strains with extracellular replication, are particularly representative. These bacteria have in fact a capsule of large size which only permits effective phagocytosis by macrophages. This mechanism applying non-specific agents, the results obtained with Klebsiella may be extended to micro-organisms which replicate in the same manner.

An experimental procedure was studied by CHEDID L. et coll. in "Proc. Natl. Acad. Sci. USA," 1977, 74: 2089, which permits the stimulating effect or not to be observed of substances studied with regard to immune defenses according as they protect or not the mice to which they are injected, the mice being inoculated by a dose of *Klebsiella pneumoniae* which results in the death of almost all of the controls.

When it is desired to study the effects of such substances on infections whose agents multiply intracellularly, the Listeria are among the micro-organisms most used, and notably *Listeria monocytogenes*. The latter are the basis of biological tests which have become classical, both for the study of specific and non-specific reactions.

By way of example, may be mentioned the experimental procedure described by MEDINA, VAS and ROBSON (J. Immunol., 1975, 114, 1720), which permits the stimulant or non-stimulant effect to be observed of substances studied with regard to immune defenses, according as they protect or not mice into which they are injected against a dose of *Listeria monocytogenes* which results in the death of almost all of the controls, or according as they result or not in the short-term destruction of said micro-organisms.

It is more and more affirmed today that cell mediated immunity constitutes a complex defense system of organisms coming into play in numerous situations, not only with respect to intracellular micro-organisms but also with respect to neoplastic growth and the multiplication of numerous fungal, parasitic agents, etc.; it is this system which also is responsible in the rejection of grafts and numerous auto-immune processes.

In a general way, reference may be made, as regards all of the above-mentioned problems, to, for example, the articles of Priscilla A. CAMPBELL, entitled, "Immunocompetent Cells in Resistance to Bacterial Infections", which appeared in "Bacteriological Reviews", June 1976, p. 284–313, of G. B. MACKANESS, entitled "Cellular Immunity", which appeared in the Annals of the Pasteur Institute, 1971, 120, 428–437, of G. H. WERNER et coll., entitled "Toxicological Aspects of Immunopotentiation by Adjuvants and Immunostimulating Substances", which appeared in the Bulletin of the PASTEUR INSTITUTE, volume 75, No. 1 of January 1977, and in a report of a scientific group of the World Health Organization, entitled "Responses immunitaires a support cellulaire", which appeared in "Org. mond. Sante, Ser. Rapp. techn., 1969, No. 423.

It results from the foregoing that the placing at the disposal of specialists, notably of the biologist and of the clinician, of compositions or products capable of stimulating immunitary defenses of the above-indicated types, can have capital importance for both the study of other substances at the research level, both fundamental and applied, and in the domain of human or veterinary therapeutics.

Certain agents are already known which are capable of stimulating non-specifically these various immunitary responses, both for cellular mediation and for humoral mediation. Thus, for example, bacterial lipopolysaccharides (LPS), are known for their protective activity with respect to humoral or cellular infections. The LPS possess, in addition, non-specific immunological adjuvant properties, in that they facilitate an increase in the ratio of specific antibody synthesis by an organism subjected to antigen aggression, of any nature.

It is known in the same way that mycobacteria, and more particularly "Calmette-Guerin bacillus" (CGB), possess powerful non-specific immunostimulating properties.

However, there can be no question of contemplating the utilization of LPS in therapeutics, considering their extreme toxicity which is well known. CGB itself is not free of numerous drawbacks, which can be demonstrated, for example, in the animal, notably at the level of the increase in sensitivity of the host to endotoxins, of the production of a hypersensitivity to tuberculin, of the induction of granuloma, of hyperplasia of the lymphoid tissue and, notably in the rat, of polyarthritis.

It is known that numerous researchers are attached to the study of extracts capable of being obtained from mycobacteria, for the purpose of obtaining purified or detoxified agents retaining the biological properties of value of CGB or LPS, whilst being free of the above-mentioned drawbacks. The development of these researches has lead to small molecules, representing in themselves a considerable contribution to the arsenal of substances which the researcher and clinician has available, which are now acceptable to chemical synthesis, which are practically devoid of toxicity and whose very powerful immunological adjuvant activity, is manifested even when they are administered to a host, in the absence of an oily support, as was necessary as regards more particularly the fractions obtained by extraction, notably from mycobacteria.

The above-mentioned small molecules are, as is now well-known, constituted by N-Acyl-muramyl-peptides or certain of their substitution derivatives.

The most representative product of the series of the N-acyl-muramyl-peptides is constituted by N-acyl-muramyl-L-alanyl-D-isoglutamine (MDP). Various researches have however shown that the immunological adjuvant activity can be maintained, to a greater or lesser extent, by the introduction of various substituents into the muramyl group or by the replacement of the first aminoacyl residue by others, derivatives of various amino acids of the L series.

It has already been observed for certain of the muramyl peptides of the type concerned, and more particularly as regards N-acetyl-muramyl-L-alanyl-D-isoglutamine already mentioned (MDP) or for the corresponding non-amidated derivative, namely N-acetyl-muramyl-L-alanyl-D-glutamine (MDPA) or again $\alpha$-esters of MDPA, that they possess also anti-infectious properties which are already very considerable, which are manifested more particularly at the level of the humoral immunity mechanisms. Recently it has also been observed that there is an activity of certain lipophile derivatives on infections of the endocellular type such as those caused by Listeria.

The invention results from the discovery that novel products, constituted by several molecules of compounds of the muramyl-peptide type coupled in the form of an oligomer, have also excellent properties for the stimulation of immune responses.

The products according to the invention are quite distinct from previously known water-soluble natural adjuvant products and which can be obtained from the cellular walls of micro-organisms, such as mycobacteria. In fact, the latter, which include in their structure at least one peptidoglycane fragment, have glucosamine units, and more particularly N-acetyl-glucosamine, which units are absent from the novel products according to the invention.

Again with respect to the prior natural products derived from the walls of micro-organisms, the novel products can have the advantage of manifesting their properties even when they are administered in a oily phase.

With respect to the previously described monomeric products, the oligomer compounds can also have certain advantages. The first advantage is connected to the fact that the use of molecules of high molecular weight can result in slower resorption in the individual to which they are administered. The prolonged effect thus-obtained can be accompanied by an increase in responses of the treated subject with respect to those which result from the same dose of monomer agent. Another advantage is bound up with their molecular size which results in their phagocytosis, thus stimulating the cells responsible for this effect. Another advantage also is the possibility for the oligomer compounds according to the invention, with equal activity, of modifying the secondary characters of the monomers used; in particular, it is possible to obtain oligomer compounds whose administration does not have troublesome secondary effects and which, for example, have an attenuation, even a disappearance of the pyrogenic character. The passage of the monomers to polymers can also result in changes in certain types of activity, as will become apparent in the examples of the application, with respect notably to β-D-p.aminophenylglycoside of MDP.

For all these reasons, the oligomers according to the invention are novel products of great interest, both from the point of view of pharmaceutical use and from that of laboratory reactants. The novel products according to the invention are oligomers whose monomer elements are muramyl-peptides or derivatives of the latter. These monomers have a group derived from muramic acid to the carboxyl of which is fixed a peptide chain comprising at least two aminoacyl residues. The first aminoacyl is one of the group comprising L-alanyl, L-arginyl, L-asparagyl, L-cysteinyl, L-glutaminyl, glycyl, L-histidyl, L-hydroxyprolyl, L-isoleucyl, L-leucyl, L-methionyl, L-phenylalanyl, L-prolyl, L-seryl, L-threonyl, L-tryptophanyl and L-valyl. The second aminoacyl is a D-glutamyl or D-isoglutaminyl residue. The oligomers according to the invention are for the most part soluble in water and are in addition characterized by the fact that they do not have, in their structure N-acetyl-glucosamine units.

Preferably, the oligomers according to the invention have a molecular weight, or an average molecular weight when it relates to products which are only defined statistically, which does not exceed about 25,000.

According to another mode of characterization, the oligomers contain preferably at the most 50 muramyl-peptide units.

In the oligomers according to the invention, it is preferable that, in each molecule, the ratio of the total number of aminoacyl units to the total number of muramyl units be at least equal to 7.

The oligomers according to the invention may be constituted by an assembly of muramyl-peptide monomers to one another, bringing into play the reactive functions that they can include. They may also be formed by the coupling of muramyl-peptide monomers by means of "bridging" agents.

On the hypothesis that the assembly of monomers is obtained, at least in part, by means of a bridging agent, it is preferable that the proportion of residues corresponding to this agent, which are to be found in the oligomer, be such that they do not represent more than 60% of the total weight of the molecule.

For certain applications of the products according to the invention, and in particular when they are used for their immunity adjuvant properties, it is preferable that these products should not themselves be generators of immune reactions, in other words that these products should not be immunogenic. In practice, it suffices that this non-immunogenic character be observed under conditions useful for the manifestation of their adjuvant activity.

For this same reason, in muramyl-peptide monomers forming the oligomer, those are preferred for which the first aminoacyl residue fixed to the muramyl group does not contain an aromatic nucleous. This residue is consequently selected preferably from among: L-alanyl, L-arginyl, L-asparagyl, L-cysteinyl, L-glutaminyl, glycyl, L-histidyl, L-hydroxyprolyl, L-isoleucyl, L-leucyl, L-methionyl, L-prolyl, L-seryl, L-threonyl and L-valyl.

The structure of the oligomers according to the invention is not known with exactitude in all cases, and certain among them, such as that already indicated, can only be defined statistically. It is however possible, even in the latter case, to formulate some hypotheses on the manner in which the monomers are coupled to one another or are connected together by means of bridging agents, considering the functional groups of the monomers which can enter into reaction. These functional groups are, in the most usual monomers, carboxyl, amine or hydroxyl functions.

The one or more reactive functional groups are arranged on the peptide part of the monomer and/or in position 1, 2, 4 or 6 of the oside residue of the muramyl group, or on substituent groups occupying these same positions.

According to an advantageous embodiment of the invention, the oligomer is formed by the assembly of two or more monomers, coupled together through their peptide portion, by linkages also of the peptide type. It is thus possible to produce oligomers according to the invention by connecting the monomers through aminoacyl residues or peptidyl residues serving as a briding agent.

According to a preferred embodiment, oligomers according to the invention are produced by "bridging" monomer units of muramyl-peptide by means of lysine or of peptide chains including lysyl residues.

The monomers may also be coupled to form the oligomer according to the invention by means of polyfunctional bridging agents such as those which are used for the bridging of proteins.

Advantageous bridging agents are constituted notably by dialdehyde or diacid compounds, or again by derivatives of the latter such as their activated diesters. It is also possible to use polyfunctional agents such as dimethyl adipimidate or homologous compounds and derivatives of the latter.

A particularly preferred bridging agent is constituted by gluteraldehyde, known in the prior art for its ability to cross-link proteins.

Preferably, monomers suitable for the formation of the oligomers according to the invention are muramyl peptides corresponding to the general formula

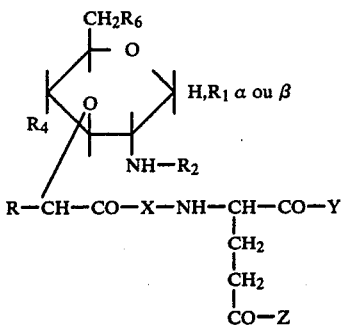

$$R-CH-CO-X-NH-CH-CO-Y \quad (I)$$
$$| \quad\quad\quad\quad\quad\quad\quad\quad\quad CH_2$$
$$\quad\quad\quad\quad\quad\quad\quad\quad\quad\quad CH_2$$
$$\quad\quad\quad\quad\quad\quad\quad\quad\quad\quad CO-Z$$

in which the substituents R, $R_1$, $R_2$, $R_4$, $R_6$, X, Y and Z have one of the following significances:

R is either a hydrogen atom, or an alkyl group comprising 1 to 4 carbon atoms, $R_1$ is either —$NH_2$, or —OH, or a radical resulting from the substitution of a hydrogen of the latter by an alkyl or aryl radical having at the most 10 carbon atoms, which can carry functional groups, $R_2$ is a hydrogen atom or an acyl radical which can bear functional groups and including at the most 22 carbon atoms, $R_4$ is a hydroxyl or the group resulting from the substitution of the hydrogen of the hydroxyl by an acyl or alkyl radical comprising at the most 4 carbon atoms, $R_6$ is either —$NH_2$, or —OH, or the group resulting from the substitution of a hydrogen of one of the latter by a saturated or unsaturated acyl or alkyl radical, possibly cross-linked, substituted or not, containing from one to about 90 carbon atoms, and which can also carry functional groups: hydroxyl, carboxyl, carbonyl, amino, cyclopropane, methoxy, X is one of the aminoacyl residues L-alanyl, L-arginyl, L-asparagyl, L-cysteinyl, L-glutaminyl, glycyl, L-histidyl, L-hydroxyprolyl, L-isoleucyl, L-leucyl, L-methionyl, L-phenylalanyl, L-prolyl, L-seryl, L-threonyl, L-tryptophanyl and L-valyl, Y is either —OH, or an alkoxy radical comprising from 1 to 4 carbon atoms, or —$NH_2$, the hydrogens of the amino group being substitutable by alkyl residues of 1 to 4 carbon atoms, or an amide aminoacyl residue, Z is either —OH, or —$NH_2$, or a group of the formula —$(A)_n$—W—R', with n either zero, or 1, 2 or 3, or —$(A)_{n'}$—A'—CO—R' with n' either zero, or 1 or 2, in which A is an aminoacyl residue of the group indicated above for X, it being understood that the A groups present in the same compound may be identical or different, n only representing the total number of A groups in this compound, A' is an aminoalcohol residue

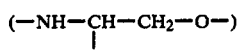

corresponding to the aminoacyl

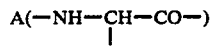

indicated above,

W is either oxygen, or an —NH group,

R' is a hydrogen atom or a linear or branched alkyl residue, saturated or not, which can carry functional groups hydroxyl, carbonyl, carboxyl, cyclopropane, methoxy, or an aryl or alkyl-aryl residue, possibly substituted.

Certain of the compounds corresponding to the general formula (I) have advantageous aspects. Below are indicated the various significances of the variable elements of the formula (I) corresponding to the preferred structures.

In this formula, the second aminoacyl group of the peptide chain connected to the residue of the muramyl type is the D-glutamyl residue. The first aminoacyl group (denoted by X) may, on the other hand, be selected from among the various aminoacyl residues mentioned above. Among the monomers of formula (I), those are preferred in which the first aminoacyl residue is L-alanyl. A second type of preferred monomer is that in which this aminoacyl is L-seryl. Another type of preferred compound is that in which this aminoacyl is glycyl.

The monomers in which the first aminoacyl residue is L-prolyl, L-threonyl or L-valyl, are also advantageous.

When at least one aminoacyl (A) figures in Z, it is preferred that the first fixed in the γ position of the glutamyl residue should be an L-lysyl, L-alanyl or L-glutamyl residue. Preferably also, when an aminoalcohol residue (A') occurs in the formula, the preferred residues are those corresponding to lysine, alanine and glutamic acid.

At the α position of the D-glutamyl residue, the possible variants or substitutions are more limited than in the γ position of this same residue. The Y substituent can firstly represent —OH, that is to say that the free carboxylic function of the glutamic acid is to be found. It can also be the amide form of this residue, that is to say the isoglutaminyl form, when Y is —$NH_2$, one at least of the hydrogen atoms of this group being substitutable by short alkyl residues comprising from 1 to 4 carbon atoms. Esterified forms of the acid can also be present, Y then being an alkoxy, comprising 1 to 4 carbon atoms.

In a preferred form, Y is hydroxyl.

In another preferred form, Y is —$NH_2$.

Another preferred form is constituted by the case where Y is either —$OCH_3$, or —$OC_2H_5$.

In the most usual preferred form, that is to say that for which the structure of the muramic acid is to be found, R is —$CH_3$. In another preferred form, the group R is a hydrogen; the structure is then that of the homologue denoted by the name nor-muramic acid. Finally, in another preferred form, R is —$C_2H_5$; to this form corresponds the so-called homo-muramic structure.

The glycoside linkage of the saccharidic portion in the monomers according to the invention may be represented in the anomeric forms α or β. The functional groups of the oside residue may also receive various substituents of which the prior art, relating to adjuvant agents of the muramyl-peptide type, has given a certain number of examples. In particular, the literature describes products of which the hydroxyl functions of the oside residue are esterified or etherified, or the amine function in the 2 position is acylated.

In the general formula (I), the substituents of the glucopyranoside ring have been denoted by $R_1$, $R_2$, $R_4$ and $R_6$. The various positions do not present the same possibilities of substitution, the 6 position being that to which the greatest latitude is offered.

Preferred monomers are those in which one or several of the substituents $R_1$, $R_4$, and $R_6$, independently of one another or simultaneously, are a hydroxyl.

Advantageous monomers are also those for which $R_1$ is —$NH_2$, —O—$C_2H_4$—$NH_2$ (aminoethoxy) or —O—$C_6H_4$—$NH_2$ (paraminophenyloxy).

Advantageous monomers are equally those for which $R_4$ corresponds to the acetic or monosuccinic esters.

Preferred monomers are those for which $R_6$ is an amine function, or again an ester, whose acyl residue contains from 1 to 6 carbon atoms, in particular the acetic or monosuccinic esters. $R_6$ is also advantageously the ester corresponding to the mycolyl (about $C_{80}$ to $C_{90}$) or corynomycolyl ($C_{32}$) groups.

In the preferred monomers, $R_2$ is an acetyl group (—CO—$CH_3$) or a hydrogen).

Particularly preferred monomers for the constitution of the oligomers according to the invention are:
N-acetyl-muramyl-L-alanyl-D-isoglutamine and its esters,
N-acetyl-muramyl-L-alanyl-D-glutamic acid, its diamide, its α esters, and methyl, ethyl, propyl diesters,
N-acetyl-muramyl-L-alanyl-D-glutamine and its methyl, ethyl, propyl esters.

Other advantageous monomers are:
N-acetyl-muramyl-L-seryl-D-isoglutamine,
α-glycidyl amide of N-acetyl-muramyl-L-alanyl-D-glutamic acid,
N-acetyl-muramyl-L-alanyl-D-isoglutaminyl-L-lysine and its methyl and ethyl esters,
N-acetyl-muramyl-L-alanyl-D-isoglutaminyl-L-alanine,
N-acetyl-muramyl-L-alanyl-D-isoglutaminyl-L-lysyl-L-alanine,
4,6-di-O-acetyl-N-acetyl-muramyl-L-alanyl-D-isoglutamine,
6-O-succinyl-N-acetyl-muramyl-L-alanyl-D-isoglutamine,
methyl ester of 4,6-di-O-succinyl-N-acetyl-muramyl-L-alanyl-D-isoglutamine,
methyl-ester of 4-O-acetyl-6-O-($N^\alpha$ lysylamide)-succinyl-N-acetyl-muramyl-L-alanyl-D-isoglutamine.

An advantageous oligomer according to the invention is constituted by two monomers of formuls I in which $R_1$, $R_4$ and $R_6$ are simultaneously a hydroxyl, $R_2$ is —CO—$CH_3$, R is —$CH_3$ or H, X is an L-alanyl, L-seryl, or glycyl residue, Z is —OH, the two monomers being fixed through their carboxyl at the α position of the D-glutamyl residue to the amine functions of the same lysine residue. A particularly preferred oligomer of this type is the dimer of formula

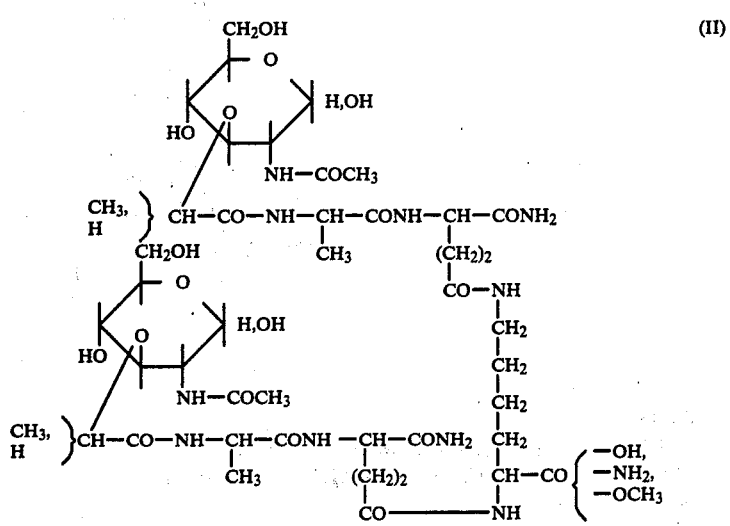

that we will denote in its abridged form $(MDP)_2$-Lys-(—OH, —$NH_2$, —$OCH_3$) or nor $(MDP)_2$-Lys-(—OH, —$NH_2$, —$OCH_3$).

According to another preferred type of oligomer, monomers of formula I are attached to a peptide chain constituted by lysine units, equal at least in number to that of the muramyl-peptides contained in said oligomer. A preferred oligomer of this type is constituted by a trimer of the formula.

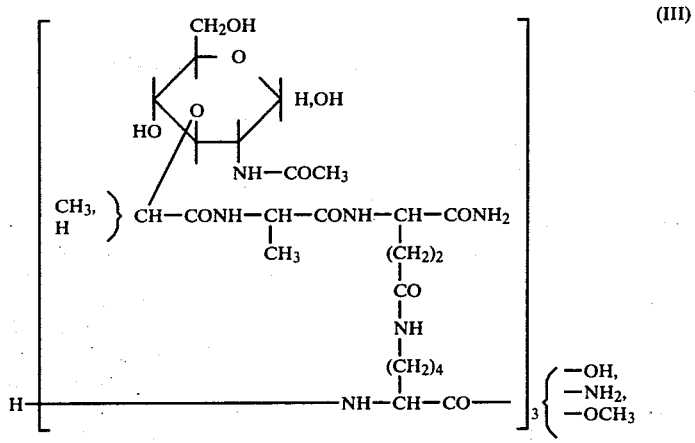

(III)

in which the terminal carboxyl of the peptide chain is either free, or amidated, or is esterified. We will denote the esterified product by the abbreviation (MDP)₃-Lys-(—OH, —NH₂, —OCH₃) or nor(MDP)₃-Lys-(—OH, —NH₂, —OCH₃).

Another preferred type of oligomer is constituted by dimers of compounds of formula I bridged by a diacid compound such as succinic acid, or by a difunctional bridging agent such as dimethyl adipimidate or its homologues and their derivatives, notably their esters. Residues of bridging agents similar to the adipimidyle residue are notably those of the formulae

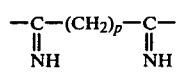

with p comprised between 2 and 10, in particular, p = 4 or

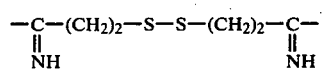

Belonging to this last type of compounds is the dimer of N-acetyl-muramyl-L-alanyl-D-isoglutaminyl-L-lysine (or the corresponding nor-muramyl compound) bridged by the adipimidyl residue and of the formula

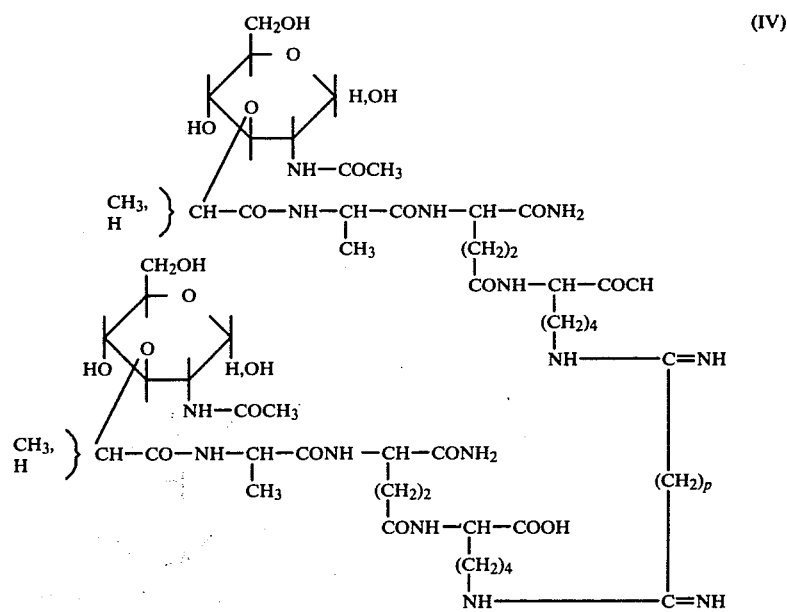

(IV)

An other type of preferred oligomer compound is obtained from monomers of formula I having at least one reactive amine function, notably on the oside residue, in position 1, 2, 4 or 6, the monomers being bridged by means of glutaraldehyde. The preferred compounds are obtained from β-D-p.aminophenyl glycoside of N-acetyl-muramyl-L-alanyl-D-isoglutamine (abridged PAP-MDP), and more particularly the oligomers containing on the average from 8 to 10 monomers per molecule.

The identification of oligomer compounds according to the invention requires various analysis techniques habitually used for the study of complex molecules, notably for the study of proteins and carbohydrates.

On the complete molecule, it is possible to use methods of determining molecular weights, spectroscopic studies, chromatographic studies . . . . A complete identification necessitates mostly a prior fragmentation of the molecules by the usual methods of hydrolysis. Fragmentation can lead to the release of the monomer units of muramyl-peptide. Nonetheless, mostly, the fragmentation leads to a group of smaller elements which are notably the constituent amino acids, the acids corresponding to the acyl residues, etc., which are themselves identified according to the traditional methods. The combination of the properties of the oligomer and the knowledge of the constituent elements then permits reconstitution of the structure of the oligomer under study. Obviously, of course, in the case of products of variable structure, as is the case for the oligomers obtained with glutaraldehyde as bridging agent, only a statistical formulation can be deduced from the analysis.

The products according to the invention are prepared by synthesis. If necessary, certain of the "fragments" used for the synthesis can be derived from natural products.

To arrive at the same monomer, various routes are possible. In all cases, the synthesis includes a series of steps in the course of which the various "fragments" constituting the structure of the whole of the compounds according to the invention are progressively assembled. The principal differences between the possible routes are in the sequence chosen for the assembly of the fragments. The reaction methods leading to the fastening of one fragment to the one or more contiguous fragments are on the whole little modified by the order in which this integration is conducted, it being well understood that this order depends, on the one hand, on the selection of functional groups which react and which, consequently, must be freed for the step concerned, and on the other hand, the choice of the groups which must be blocked in order not to intervene in the course of this same step.

The preparation of the monomers can be done from the corresponding compounds of the muramyl-peptide type. The production of the latter has been described in numerous publications. If necessary, for those whose preparation does not appear expressly in the literature, notably for the various modifications corresponding to the substitutions of the muramyl group or of similar groups, they can be obtained by following the conventional methods of preparation of corresponding derivatives of oligosaccharide chemistry.

In the same way, the constitution of the peptide chain connected to the muramic acid is carried out according to traditional methods in the synthesis of peptides.

Below are given in succinct manner the main indications relating to various operations which can be applied for synthesizing the monomers of formula (1), first by envisaging each step separately, then by indicating some preferred typical sequences.

(a) Formation of muramic acid or the like

To obtain the analogues of N-acetyl-muramic acid of the formula

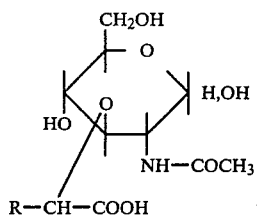

in which R has the previously indicated meaning, it is possible to start from a derivative of N-acetyl-2-glucosamine whose hydroxyls in position 1, 4 and 6 are blocked in traditional manner. The method of preparation of such a derivative, the benzyl-2-acetamido-4,6-O-benzylidene-2-deoxy-D-glucopyranoside, is described notably by P. H. GROSS and R. W. JEANLOZ (J. Org. Chem. 1967, 32, 2761).

The formation of N-acetyl-muramic acid ($R = CH_3$) or of one of its analogues can be effected in the way described in French Patent Application Nos. 74 22909 or 76 19236 (respectively, for these applications, $R = CH_3$ and $R = H$) taking the method described by OZAWA and JEANLOZ (J. Org. Chem., 1965, 30, 448).

This formation comprises, for example, the preparation of sodium salt of the hydroxyl at the 3 position and the subsequent condensation of the sodium derivative with the salt or the ester of an α halogenated acid such as 2-chloro-propionic acid or chloroacetic acid to take up again the case of the two previously indicated patent applications. The halogen compound used in the L form can be prepared by the method described by SINAY et al (J. Biol. Chem. 1972, 247, 391). By using the appropriate halogenated acids, it is possible to prepare all the derivatives corresponding to the various significances of R. Thus, to introduce an R group with 4 carbons, the salts or esters of 2-chloro-butyric acid may be used.

When a halogenated acid ester is utilized, in order to be able to proceed with the subsequent peptide condensation, the carboxylic function may be freed by suitable hydrolysis.

(b) Substitution on the saccharide residue

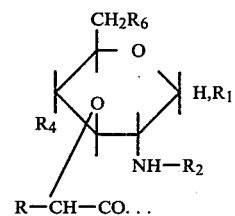

Starting from N-acetyl-muramic derivatives blocked in the 1, 4, 6 positions as obtained in (a), it is possible to prepare the various analogous compounds in which the acetyl group fixed to the nitrogen at the 2 position is replaced by substituents whose nature is that given in the general definition, that is to say an alkyl, aryl or alkyl-aryl group, possibly substituted and including at most 22 carbon atoms. For this modification, it is possible to carry out in known manner a hydrolysis of the acetyl by a strong base, for example as is described in the publication of P. H. GROSS and R. W. JEANLOZ indicated above.

The resulting compound, in which an amino group is in the 2 position of the glucopyranoside ring, can then be again subjected to an acylation process, under the usual conditions, with a suitable acylating agent corresponding to the $R_2$ group that it is desired to introduce. As acylating agent, it is possible notably to use the acid anhydrides or chlorides.

The substitutions at the 1, 4 and 6 position may be effected by methods which have been described previously and which are conventional in sugar chemistry. When the contemplated constituents are different from one another, as many successive substitution reactions follow as there are distinct substituents. In the course of these reactions, the positions which do not have to be substituted or those which must subsequently be the subject of another substitution are protected temporarily by blocking groups according to the usual methods.

The blocking groups initially present, in the case where one starts, as previously indicated, from benzyl-2-acetamido-4,6-O-benzylidene-2-deoxy-D-glucopyranoside, are removed, for example, by the action of the acetic acid (at 60% for 1 hour under reflux) and catalytic hydrogenation, as described, for example, by WERSER et al. (Biochem. Biophy. Res. Commun., 1975, 66, 1316), or by catalytic hydrogenation by the method of LEFRANCIER et al. (Int. J. Peptide Protein Res., 1977, 9, 249).

The methods of substitution are those traditionally used. To obtain the acylated derivatives, procedure with the aid of an acylating agent corresponding to the substituent that it is desired to introduce (anhydride, acyl chloride, etc.).

The 1, 4, 6 positions are not equivalent as regards their reactivity. The $C^6$ position is easier to substitute, also, when this position must be substituted, it is possible to operate without blocking the other positions, with an amount of substitution agent equal to that necessary for the substitution in a single position.

A particular example of the method of preparation of the derivatives substituted at the 6 position is given in the article of KUSUMOTO et al. (Tetrahedron Letters, 1976, 47, 4237).

The substitutions on the oside residue may be produced before or after fixing the peptide chain or the fragments of the latter.

(c) Peptide chain

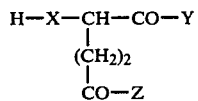

The fixing of a peptide chain to the N-acetyl-muramic acid, or to an analogue of the latter as has been indicated above, is effected by traditional methods in the field of peptide synthesis. Such methods have been amply described in the prior literature and in particular in the previously indicated French patent applications.

In general, glycopeptide syntheses can be effected either by fixing a first amino acid to the muramyl group, then by fixing to the compound thus obtained the second amino acid, and so on. It is also possible to prepare the entire peptide chain separately amino acid by amino acid and to fix the latter on the muramyl group. It is finally possible to select intermediate methods in which fragments of the chain are prepared, and then these fragments are joined together until a complete chain is formed which is then fixed to the muramyl group, or to fix a first fragment to the muramyl group, then a second to the product thus-obtained, etc. The choice of sequence is guided mainly by reasons of convenience or of yield.

The Y and Z substitutions are advantageously effected on the glutamyl group before the synthesis of the chain. In the same way, when n is different from 0, that is to say when one or several aminoacyl groups complete the peptide chain, the Z group is first fixed to the terminal aminoacyl before the latter is integrated into the peptide chain.

The peptide syntheses are carried out by traditional methods. By way of example, it is possible to use methods of activating carboxyls, like the method called mixed anhydrides. Advantageously, the peptide synthesis is carried out by means of a compound of the carbodiimide type such as N,N'-dicyclo-hexylcarbodiimide or equivalent carbodiimides. A review of the traditional methods of peptide synthesis is to be found in J. H. JONES, Chemistry and Industry, 723 (1974). It is also possible to refer to the already mentioned French patent applications, or again to the following applications: Nos. 75 29624, 76 06819, 76 06820, 76 06821, 76 21889, 77 02646 and to the article of LEFRANCIER et al. (Int. J. Peptide Protein Res., 1977, 9, 249 and 1978, 11, 289).

The formation of esterified or amidated derivatives corresponding to the group Y is obtained in known manner. It is possible, in particular, to refer to the above-indicated French patent applications, and notably to Application Nos. 76 06820, 76 06821, 76 21889 and 77 02646.

To fix the residue W—R' to the amino acid situated at the end of the peptide chain, one proceeds with activation of the carboxylic group of the amino acid in a manner known in itself, and it is subjected to alcoholysis or aminolysis by an R'OH alcohol or an R'NH$_2$ amine.

Synthesis sequences of monomers of formula I in which Z is an —OH or —NH$_2$ radical (Diagram I)

The starting product is a derivative (1), R$_1$ representing the benzyl glycoside radical, prepared as described by GROSS and JEANLOZ (J. Org. Chem., 1967, 32, 2759). To obtain the similar compound in which R$_1$ is an alkyl- or aryl-alkyl group, it is possible to use the method of preparation of the α or β-glycosides described in this same article, or any known method for such preparation in oligosaccharide chemistry.

When R$_1$ represents the p-nitrophenyl radical, it is possible notably to operate as described by PETITOU and SINAY (Carbohyd. Res., 1973, 29, 502). When R$_1$ represents the benzyloxycarbonyl-aminoethyl radical, it is possible to proceed in the manner described by KING et al (Carbohyd. Res., 1977, 55, 83). In another modification, when R$_1$ is an azide group, the introduction can be done, for example, as described by MICHAEL and KLEMER (Adv. Carb. Chem., 1961, 16, 95).

To modify the nature of the N-acyl group at the 2 position, the N-acetyl group can be hydrolyzed as described by GROSS and JEANLOZ (J. Org. Chem., 1967, 32, 2759) to result in derivatives of formula (2). These derivatives can be N-acylated selectively notably by the action of the anhydride of the carboxylic acid to arrive at derivatives of formula (3). In a preferred modification, the acyl group newly introduced (thus the benzyloxycarbonyl group) can be selectively removed in the final step of the synthesis thus freeing the amine function. Derivatives of formula (4) may be obtained from the preceding ones according to the method described by OZAWA and JEANLOZ (J. Org. Chem., 1965, 30, 448), by means of an L-α-chloroalcanoic acid.

The derivatives of formula (4) may be coupled with a dipeptide derivative of the general formula H—X—D—Glu (Z)—OY, hydrochloride, in which formula Z is —NH$_2$ or —OH. These various peptide derivatives are prepared according to the methods described by LEFRANCIER et al. (Int. J. Peptide Protein Res., 1977, 9, 249, and Int. J. Peptide Protein Res., 1978, in press). The coupling methods used to obtain the glycopeptide derivatives of formula (5) are also described in the previously mentioned articles. However, both in the synthesis of the dipeptide derivatives as in those of the derivatives of formula (5), any coupling method may be used.

The catalytic hydrogenation of the compounds of formula (5) is carried out conventionally (LEFRANCIER et al., 1977, reference cited) to end up with the compounds of formula (6), and in particular, when $R_1$ is an azide group, or a p-nitrophenyloxy group, or a benzyloxycarbonylaminoethyloxy group, or indeed again when $R_2$ is a benzyloxycarbonyl group, in compounds possessing at least one amine function such as the compounds (1) to (4), (Diagram II), in which formula $R_4$ and $R_6$ represent an alcohol function.

In a modification, the derivatives of formula (5) undergo selective debenzylidenation such as described by MERSER et al. (Biochem. Biophys. Res. Commun., 1975, 66, 13 1316) to give the derivatives of formula (7). The selective acylation of the primary hydroxyl at the 6 position of the saccharide residue can then be done directly notably by the action of a small excess of the anhydride of a carboxylic acid. Derivatives of formula (8) are obtained.

The derivatives of formula (8) may be synthesized by a totally different sequence (Diagram IV), formula (4) similar to that developed by KUSUMOTO et al. (Tetrahedron Letters, 1976, 47, 4237), from the specific tosylation of the primary alcohol of the saccharide residue. Conventionally, in oligosaccharide chemistry, this derivative enables the production of an azide group at this position.

After catalytic hydrogenation of the compounds (8) there are obtained, when $R_1$ is an azide group, or a p-nitropheyloxy group or a benzyloxycarbonyl-aminoethyloxy radical, or indeed again when $R_2$ is a benzyloxycarbonyl group, the compounds bearing at least one amine function, such as (1) to (4) (Diagram II) for which $R_4$ is an —OH function, but also in the case where $R_6$ is an azide group, with compounds such as (5) (Diagram II), for which $R_4$ is an —OH function.

In another modification, the derivatives of formula (7) are diacylated on the two hydroxyls at the 4 and 6 positions of the saccharide residue notably by the action of an excess of the anhydride of a carboxylic acid to give the compounds of formula (9) which, subjected to catalytic hydrogenation, result when $R_1$ is an azide group, or a p-nitrophenyloxy group or benzyloxycarbonyl-aminoethyloxy group, or again also when $R_2$ is a benzyloxycarbonyl group, the compounds bearing at least one amine function, such as (1) to (4) (Diagram II).

Synthesis sequences of monomers of Formula I in which $Z=(A)_n—W—R'$, n being zero (Diagram III)

In this case, when n is zero, the γ-carboxyl function of the D-glutamyl residue is engaged in an ester linkage.

One method of preparing these derivatives consists of esterifying directly the partially blocked peptide fragment BOC—X—D—Glu—(OH)—OY, (also synthesized according to the methods described by LEFRANCIER et al. (1977, 1978, references cited)), according to the method described by WANG et al. (J. Org. Chem., 1977, 42, 1286). After removal of the ter-butyloxycarbonyl (BOC) group, the derivative obtained is coupled with a derivative of the residue of the muramyl type suitably protected, corresponding to formula (1) (Diagram III) to result in derivatives of formula (2) according to the methods described in MERSER et al. (1975, reference cited), LEFRANCIER et al. (1977, 1978, references cited). After catalytic hydrogenation and the purification carried out as described in LEFRANCIER et al. (1977, 1978, references cited), the compounds of formula (3) are obtained, and in particular, if $R_1$ is an azide group, or a p-nitrophenyloxy group or a benzyloxycarbonyl-aminoethyloxy group, or indeed again, if $R_2$ is a benzyloxycarbonyl group, the compounds bearing at least one amine function such as (1) to (4) (Diagram II), in the formula in which $R_4$ and $R_6$ are an —OH function and Z corresponds to OR'.

In a modification, the derivatives of formula (2) undergo selective debenzylidenation such as described by MERSER et al. (1975, reference cited) to give the derivatives of formula (4).

Selective acylation of the primary hydroxyl in the 6 position of the saccharide residue can be done directly notably by the action of a small excess of anhydride, of a carboxylic acid. The derivatives of formula (5) are thus prepared, which results, after conventional catalytic hydrogenation, if $R_1$ is an azide group, or a p-nitrophenyloxy group or a benzyloxycarbonylaminoethyloxy group, or indeed again if $R_2$ is a benzyloxycarbonyl group, in compounds bearing at least one amine function such as (1) to (4) (Diagram II), in the formula of which $R_4$ is an —OH function and Z corresponds to OR'.

These derivatives can be synthesized according to a totally different sequence (Diagram IV), formula (5) similar to that developed by KUSUMOTO et al. (1976, reference cited), through the specific tosylation of the primary alcohol function. This intermediate enables an azide group to be produced at this position and for this reason, after catalytic hydrogenation, a compound bearing an amine function, such as (5) (Diagram II), in which formula $R_4$ is an —OH function and Z corresponds to OR'.

In another modification, the derivatives of formula (4) are diacylated on the hydroxyls at the 4 and 6 positions of the saccharide residue by the action notably of an excess of the anhydride of a carboxylic acid to obtain finally the compounds of formula (7) which give, after catalytic hydrogenation, if $R_1$ is an azide group or p-nitrophenyloxy group or a benzyloxycarbonyl-aminoethyloxy group, or indeed again if $R_2$ is a benzyloxycarbonyl group, the compounds bearing at least one amine function such as (1) to (4) (Diagram II), in the formula of which Z corresponds to OR'.

Synthesis sequence of monomers of formula I in which $Z=—(A)_n—W—R'$ or $Z=(A)_{n-1}—A'—CO—R'$, n being 2 or more The Diagram (V) represents a sequence type of reactions resulting in the obtaining of peptide derivatives corresponding to the part Z of the general formula, namely $Z=—(A)_n—W—R'$, in which $—(A)_n—$ corresponds to 1 or 2 amino acid residues, W to oxygen or to —NH—, R' to an alkyl radical.

The N-protected derivative of the first amino acid ($N^\alpha$-ter-butyloxycarbonyl—$A_1$—OH, or BOC—$A_1$—OH, for example) is esterified by an alcohol according to the method of WANG et al. (1977, reference cited) to give after removal of the BOC group, H—$A_1$—OR' ($Z_1$).

However, in the case where R' is an alkyl residue with a chain of 4 to 20 carbon atoms, the conventional methods of esterification of the amino acids are advantageously used to obtain H—$A_1$—OR' ($Z_1$). This derivative is then coupled according to well known methods with a second amino acid residue suitably protected to give, after removal of the temporary protecting group of the α-amine function, a dipeptide compound of formula H—A$_2$—A$_1$—OR' (Z$_2$).

In the same way, an active ester such as BOC—A$_1$—OR" (R" being a p-nitrophenylic ester for example), may be amminolysed to give after deprotection of the α-amine function H—A$_1$—NH$_2$ (Z$_3$) which, according to the reaction sequence described below, results in the dipeptide derivatives of formula H—A$_2$—A$_1$—OR' (Z$_4$).

In the same way, the activated ester BOC-A$_1$—OR" may be, for example, amminolyzed by an alkylamine to give, after deprotection of the α-amine function, H—A$_1$—NH—R' (Z$_5$) which, according to the reaction sequence described below, results in the dipeptide of formula H—A$_2$—A$_1$—NH—R' (Z$_6$).

In a modification, corresponding to the case where in the formula Z=—(A)$_n$—W—R', W is an oxygen atom and R' is a hydrogen atom, the group esterifying the derivative H—A$_2$—A$_1$—O (Z$_2$) is selected so that it can be removed selectively at the end of the synthesis.

A modification of the preceding reaction sequence is described in Diagram VI and corresponds to the preparation of compounds in which Z is —(A)$_{n-1}$—A'—COR', with A corresponding to an amino acid residue, A' to an aminoalcohol residue and R' to an alkyl residue.

For this modification, an N-protected derivative of an amino acid such as BOC—A'—COOH is selectively reduced to its aminoalcohol derivative BOC—A'—CH$_2$OH according to well known methods. The amino acid can also be reduced to its corresponding aminoalcohol, then acylated selectively at its amine function according to currently used methods in peptide synthesis. The alcohol function thus created can then be esterified by an acid (R'—COOH) according to the method of esterification described by WANG et al. (1977, reference cited). This ester may also be made notably from the chloride or from the anhydride of the acid.

The synthesis of the glycopeptide derivatives corresponding to the modification of the general formula in which n is 1 or 2 is succinctly described in Diagram VII.

The partially protected dipeptide fragment BOC—X—D—Glu—(OH)—Y is prepared according to the methods described notably by LEFRANCIER et al. (1977, 1978, references cited), then coupled with the peptide derivative, represented by Z, of which we have just given the preparation for its two modifications.

After removal of the BOC group, the product obtained is coupled with a suitable derivative of the muramic acid type (1), which is that of which the synthesis is described in Diagram (I) (derivative 4) to obtain the compounds of formula (2).

After catalytic hydrogenation, the compounds of formula (3) are obtained and in particular if R$_1$ is an azide group or a p-nitrophenyloxy group or a benzyloxycarbonyl or aminoethyloxy group, or indeed when R$_2$ is a benzyloxycarbonyl group, or again if —A— corresponds to an N$^\epsilon$-benzyloxycarbonyl-lysyl residue, the compounds bearing at least one amine function such as (1) to (4) and (6) (Diagram III), in which formulae R$_4$ and R$_6$ are —OH functions.

In a modification, the derivatives of formula (2) undergo selective debenzylidenation such as described by MERSER et al. (1975, reference cited) to give the derivatives of formula (4). Selective acylation on the primary hydroxyl at position 6 of the saccharide residue can then be produced as described in Diagrams (I) and (IV). Thus as previously described, it is possible to substitute this position by an azide group. Finally the compounds of formula (6) are obtained after catalytic hydrogenation, and in particular, if R$_1$ is an azide group or a p-nitrophenyloxy group or a benzyloxycarbonylaminoethyloxy radical or indeed again when R$_2$ is a benzyloxycarbonyl group, or again if —A— corresponds to an N$^\epsilon$-benzyloxycarbonyl-lysyl residue, the compounds bearing an amine function such as (1) to (4) and (6) (Diagram III), in which formulae R$_4$ is an alcohol function.

In another modification, the derivatives of formula (4) are diacylated on the two hydroxyls at positions 4 or 6 of the saccharide residue as described in Diagram (I). After catalytic hydrogenation, the compounds of formula (7) are obtained, and in particular, if R$_1$ is an azide group, or a p-nitrophenyloxy group or a benzyloxycarbonylaminoethyloxy group or indeed if R$_2$ is a benzyloxycarbonyl group, or again if —A— is an N$^\epsilon$-benzyloxycarbonyl-lysyl residue, the compounds bearing amine functions such as (1) to (4) and (6) (Diagram II).

DIAGRAM (I)
SYNTHESIS SEQUENCES OF GLYCOPEPTIDE COMPOUNDS CORRESPONDING TO THE MODIFICATION OF THE GENERAL FORMULA IN WHICH Z IS AN —OH OR —NH$_2$

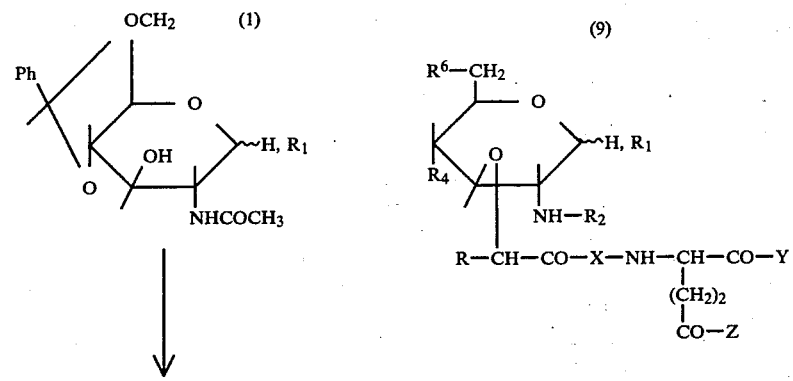

-continued
DIAGRAM (I)
SYNTHESIS SEQUENCES OF GLYCOPEPTIDE
COMPOUNDS CORRESPONDING TO THE MODIFICATION
OF THE GENERAL FORMULA IN WHICH Z IS AN —OH
OR —$NH_2$
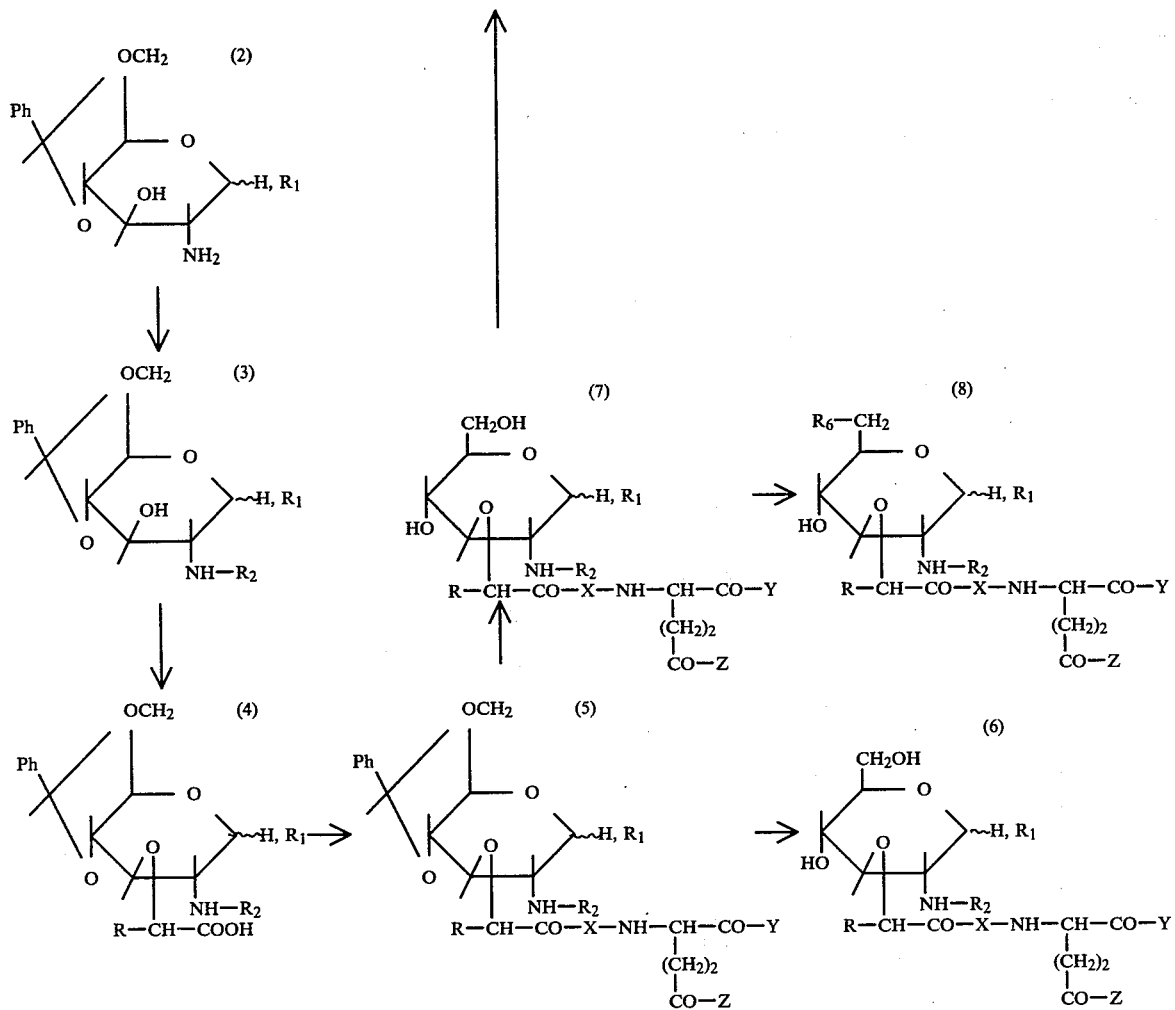
DIAGRAM (II)
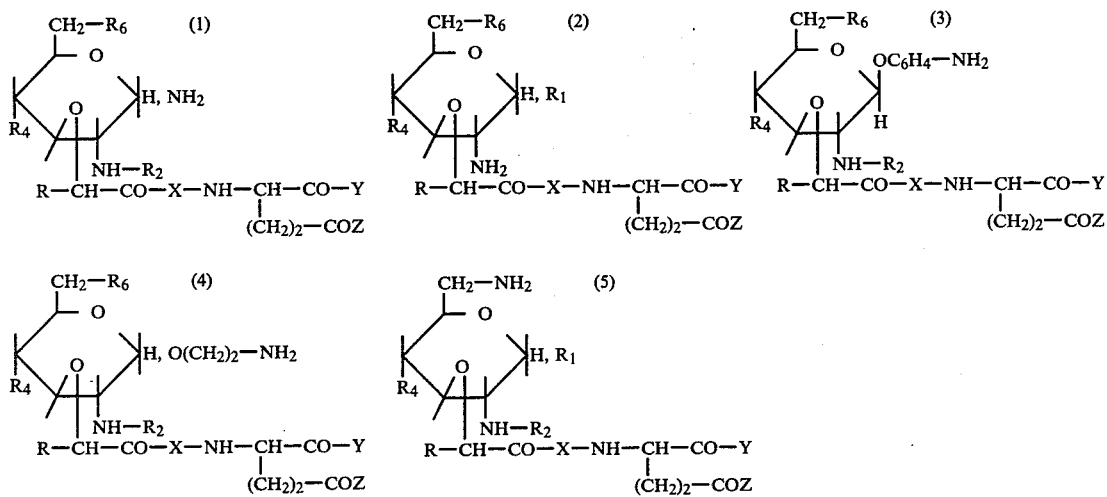

-continued
DIAGRAM (II)
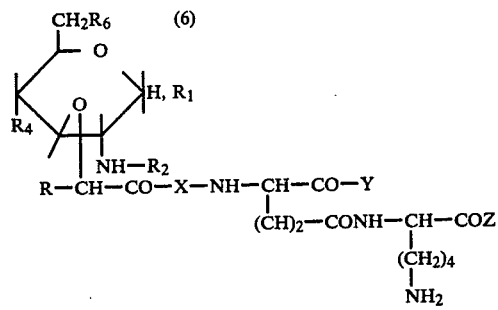
DIAGRAM (III)
SYNTHESIS SEQUENCES OF GLYCOPEPTIDE COMPOUNDS CORRESPONDING TO THE MODIFICATION OF THE GENERAL FORMULA IN WHICH Z = (A)$_n$—W—R', n being zero
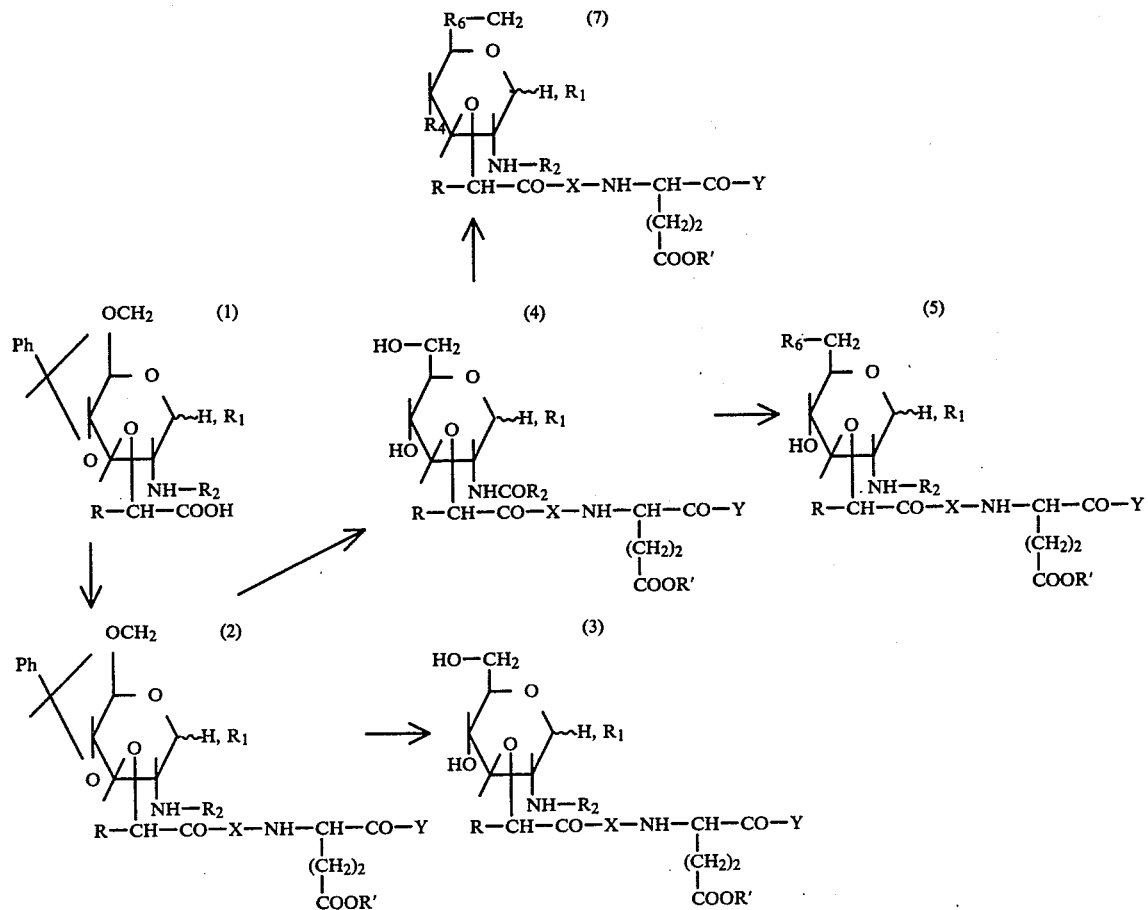

DIAGRAM (IV)
SYNTHESIS SEQUENCE OF GLYCOPEPTIDE DERIVATIVES CORRESPONDING TO THE GENERAL FORMULA AND OF WHICH THE HYDROXYL AT THE C6 OF THE SACCHARIDE RESIDUE IS ACYLATED BY A LONG CHAIN FATTY ACID
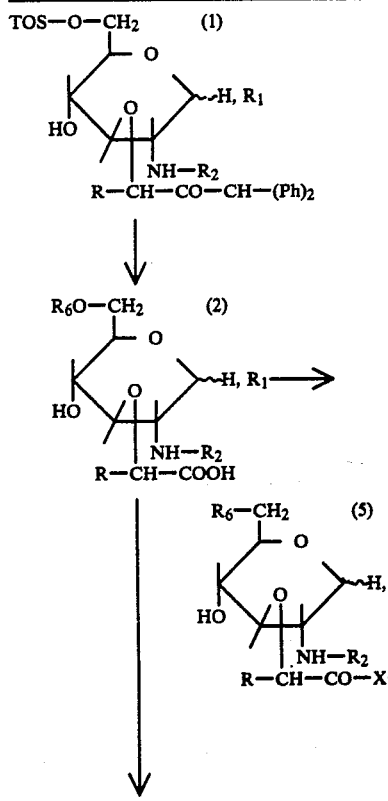
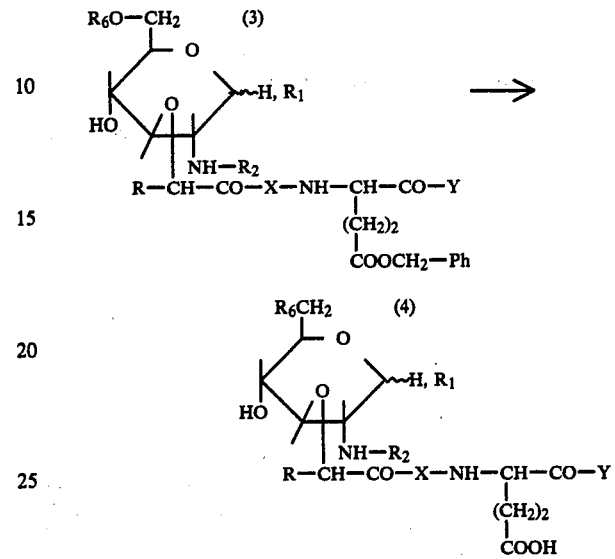
DIAGRAM (V)
REACTION SEQUENCE OF THE PREPARATION OF THE PEPTIDE DERIVATIVES OF THE GENERAL FORMULA $-Z=(A)_n-W-R_1$, WITH $n = 1$ or $2$
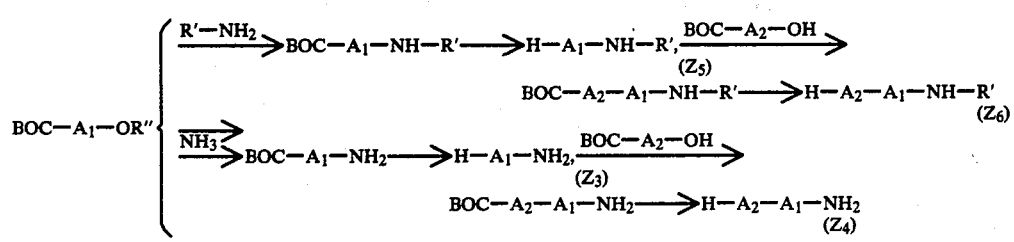
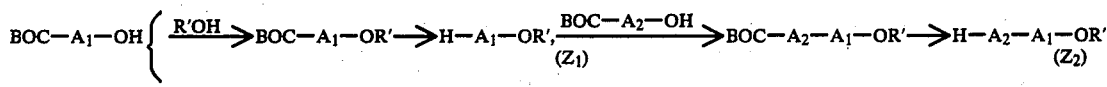

DIAGRAM (VI)

REACTION SEQUENCE OF THE PREPARATION OF PEPTIDE DERIVATIVES OF THE GENERAL FORMULA $Z = (A)_{n-1}-A'-R_1'$; $n \geq 2$.

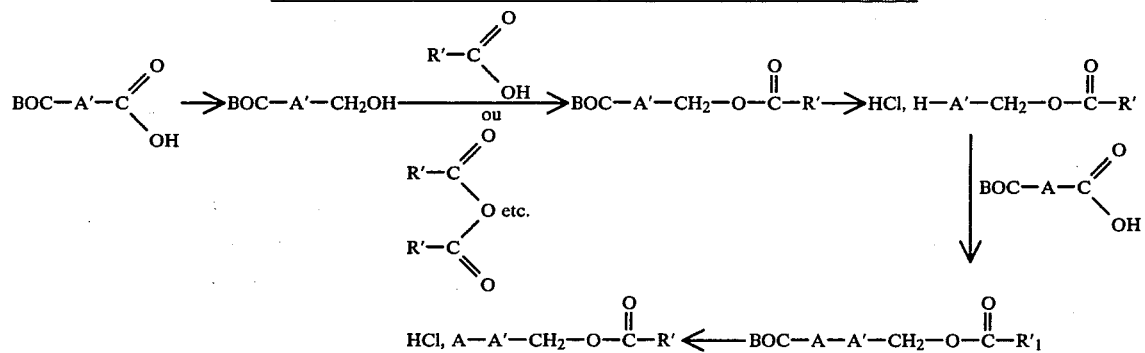

DIAGRAM (VII)

SYNTHESIS SEQUENCES OF GLYCOPEPTIDE COMPOUNDS CORRESPONDING TO THE MODIFICATION OF THE GENERAL FORMULA FOR WHICH $Z = -(A)_n-W-R'$ OR $Z = (A)_{n-1}-A'-COR'$; $n \geq 2$.

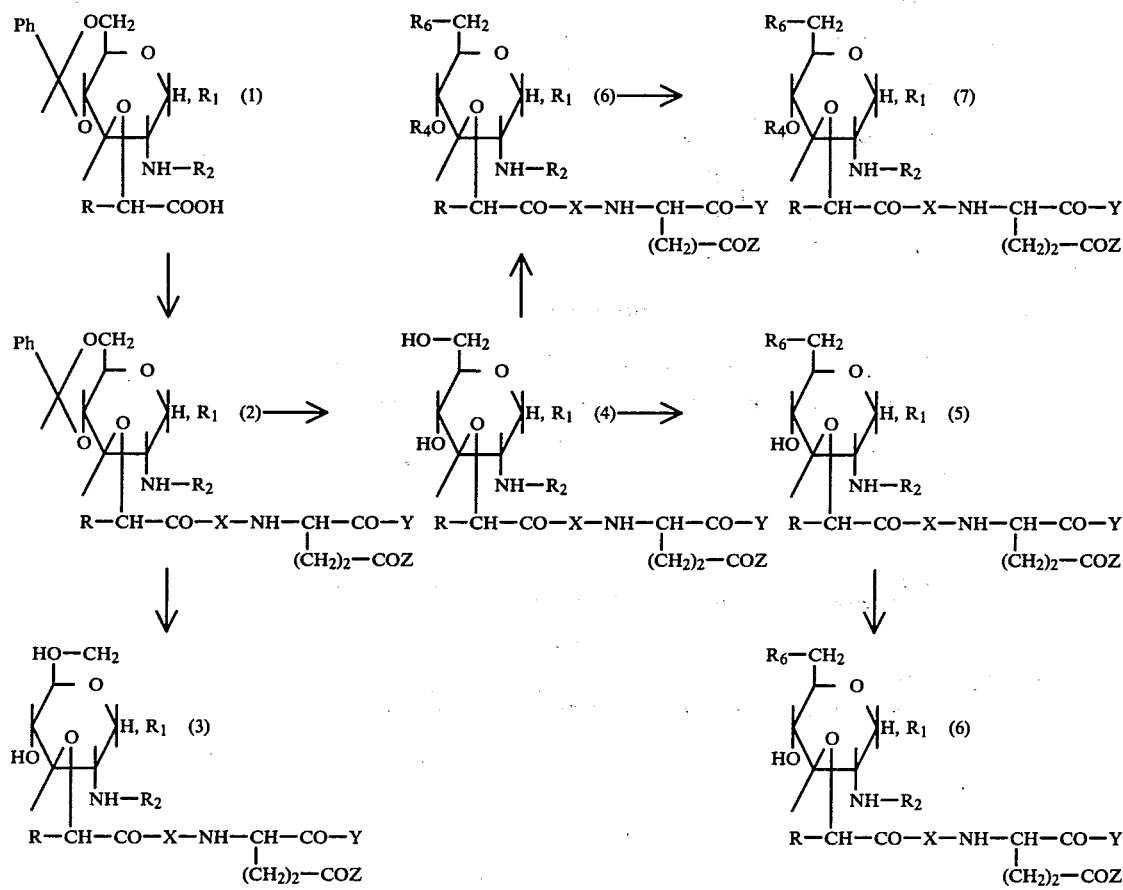

Oligomerization of muramyl-peptide type monomers, corresponding to the general formula (I)

An advantageous method of oligomerization of compounds of the muramyl-peptide type, corresponding to the general formula (I), results from the presence in their molecule, of an amine function.

Due to the fact of the polyfunctional structure of the compounds of this type, the introduction of such a function can be done at various positions corresponding to the saccharide portion or to the peptide portion, according to different reaction sequences, as has been shown below.

In the Diagram (II) are shown the formulae of six classes of derivatives, which carry an amine function and are derived from compounds of the muramyl-peptide type. These various types can be regrouped according to the manner in which the amine function appears in the monomer.

Compounds having a pre-existing amine function, either in the peptide portion, such as the compounds of formula (6), or in the saccharide portion, such as the compounds of formula (2).

Compounds possessing an amine function resulting from selective modification of one of the pre-existing functions, such as the compounds of formulae (1) and (5).

Compounds possessing a group carrying an amine function, substituting one of the pre-existing functions, such as the compounds of formulae (3) and (4).

The amine function belonging to any one of the derivatives of the various classes thus-defined may be bridged with the amine function belonging to a second molecule belonging preferably, but not exclusively, to the same class of derivatives to give, in the simplest case, a dimer. This linkage can be formed by means of any one of the so-called "bridging" reactants. Such reactants are well known and used currently in the study of interactions existing between macromolecules of a protein nature such as enzymes (see notably Methods in enzymology, S. P. KOLOWICK, N. U. KAPLAN, ed. Academic Press, Volume XXV, 1972, 585 and Fed. Proc., 1978, 37, 112).

Dimethyl adipimidate (LUBIN et al., Proc. Nat. Acd. Sci. USA, 1975, 72, 43) is thus a particularly advantageous bifunctional reactant for the preparation of dimers according to the invention. There may also be used any analogue of this reactant, of the general formula:

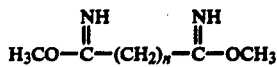

with, for example, n=6, for dimethyl suberimidate.

There may also be used all the analogous reactants of the general formula:

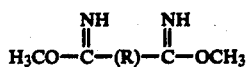

with, for example, $R = -(CH_2)_2-S-S-(CH_2)_2-$ for dimethyl-3—3'-dithiobispropionimidate.

An other type of bifunctional reactant, particularly suited for preparing dimers according to the invention, consists of a dicarboxylic acid, of which each carboxyl function can be coupled with the amine function present in the monomer according to any one of the known methods of forming the peptide linkage (carbodiimide, activated esters, etc ...).

Preferred reactants of this type are those of the general formula:

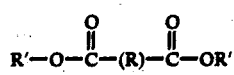

in which OR' represents an activated ester.

If $R = -(CH_2)_n-$, n=2 or 3, the reactant is a derivative of succinic acid or of glutaric acid.

If $R = -(CH=CH)-$, the reactant is a derivative of maleic acid.

Another method of producing dimers, according to the invention, corresponds to coupling, according to one of the well known methods of forming a peptide linkage, the amine function belonging to any one of the derivatives of the various classes shown in Diagram (II) with the carboxyl function present in a suitable compound of the muramyl-peptide type. This carboxyl function, according to the claims corresponding to the general formula (I), may be in the peptide portion or in the saccharide portion. Advantageously, this function occurs in the γ position of the D-glutamic acid residue. The carboxyl may also occur at the end of the peptide chain $(Z=(A)_n-W-R', R'=OH)$, but also in a side chain if, n $Z=-(A)_n-W-R'$ and $Z'=-(A)_{n-1}-A'-CO-R'$, one of the aminoacyl (A) residues corresponds to an aspartic or glutamic acid residue, finally, $R_6$ can represent $-O-CO-(CH_2)_2-COOH$ group.

More generally, the dimers such as described in the preceding paragraph may be prepared according to the procedure in use in the synthesis of polypeptides and of oligosaccharides. For this reason, and in particular by the sequential addition of suitable derivatives, it is possible to produce trimers, tetramers, etc . . . .

Derivatives possessing an amine function, which belong to any one of the classes of compounds of the muramyl-peptide type, shown in the diagram (II), but also their dimerized, trimerized, etc . . . forms, containing an available amine function, can react with glutaraldehyde to give oligomers according to a mechanism which has not been elucidated. However, the literature regarding, in particular, the preparation of protein aggregates by means of glutaraldehyde is abundant (see notably, AVRAMEAS, Immunochem., 1969, 6, 43, HARDY et al., J. Chem. Soc., Perkin I, 1976, 958).

The invention also relates to methods of using the compounds corresponding to the preceding definitions, notably as a reactant or as an active substance in pharmaceutical compositions.

The invention relates to biological reactants, for example standard immunological adjuvants, which can be constituted by means of the compounds according to the invention, notably in order to study the possible adjuvant properties of the substances under investigation, by comparison with such standard adjuvants or, on the contrary, as an agent capable of countering certain effects connected with the administration of immunosuppressive substances.

More particularly, the invention relates to medicaments including an active principle at least one of the compounds according to the invention, this medicament being applicable to control immune responses of the subject to which it is administered.

These medicaments are notably applicable when a reinforcement of the immune response to any immunogenic agent is sought. Such immunogenic agents may be natural or synthetic, and necessitate the use of a stimulating agent for the immunitary system, whether the immunogenic agent is weak in nature or whether it is strong and can be used at very small dose, or again if the immunogenic character has been reduced, for example in the course of modifications or prior purifications.

In general, the utilization of the immunoregulator compounds according to the invention is useful each time that the immunogenic agent does not permit the induction of a sufficient response.

The invention relates more particularly again to the application of the compounds concerned to the amplification of the immunogenic effect of active principles of vaccines administered to a host, animal or human, notably in the case where these vaccinating principles belong to the above-mentioned immunogenic categories of agents. Consequently, the invention relates also to pharmaceutical compositions whose active principle is constituted by at least one of the compounds according to the invention, in association with the appropriate pharmaceutical vehicle for the mode of administration required or usable having regard to the nature of the vaccinating principle used.

The invention is applied in particular to those vaccinating agents whose immunogenic character is strong but which are difficult in use in normal times by reason of too high a toxicity or undesirable side-effects. It has been confirmed that the adjuvant agents according to the invention are capable of effectively compensating for the loss in immunogenic effect which would result normally from dilution or from reduction of the doses used, notably for the purpose of reducing the toxicity or the side-effects of the abovesaid agents to a corresponding degree, and this without unfavorably influencing the latter phenomena.

The same effects are observed in the case of strong vaccinating agents of which the immunogenic character has been reduced, notably by extensive purification, to the extent where this becomes necessary for the corresponding reduction of their toxic effects or injurious secondary effects. This is particularly the case for vaccinating principles constituted by bacterial anatoxins or viral anatoxins or, generally, vaccinating principles constituted by a part only of the constituents, initially contained in the bacteria or virus against which protection is sought.

In general, the invention is applied to any antigen which has undergone chemical or physical transformations seeking to remove or modify the parts of the antigen which are responsible for its troublesome secondary effects whilst preserving the portions which are the cause of its immunogenic properties. It is to this type of weak immunogen that are attached, for example, the principles constituted by the "suo-units" derived from flu virus, and which retain only the hemagglutinins and the neuraminidases of the latter, to the exclusion of the nucleoproteins and other nucleotide constituents of the virus from which they are derived. This applies also to certain anatoxins, such as those, for example, of diptheria or of tetanus, which, as is known, may be constituted by soluble substances, such as obtained by the simultaneous action of formaldehyde and of heat on bacterial toxins derived from the corresponding bacteria.

The invention also relates to the application of the compounds according to the invention for the treatment of infectious diseases. In this application, it must be noted that the products according to the invention are clearly distinguished from the customarily used antibiotics. The products according to the invention, contrary to antibiotics, do not have a bactericidal or bacteriostatic effect in vitro. On the other hand, they can activate isolated macrophages in vitro and their action in vivo is demonstrated as will be seen in the pharmacological test examples. Unlike the antibiotics again, the action is not limited to certain varieties of micro-organisms. This is explained, as we have seen, by the fact that their activity is not direct but develops through the non-specific immunitary defense mechanisms of the host, which mechanisms their administration stimulates and amplifies. This difference in action with respect to antibiotics renders these products all the more advantageous as they can be used against pathogenic germs which have become resistant to antibiotics.

As has been seen, the mode of action of the products according to the invention approaches that of known antiinfectious compounds such as CGB or the lipopolysaccharides and since they can be employed with success for the treatment of infections without having their drawbacks, notably of toxicity, which limit or prevent the use of LPS or CGB.

The application of the products according to the invention includes both the treatment of diseases caused by extracellular growth micro-organisms such as Klebsiella (or again notably Pseudomonas, staphylococci, streptococci) and that of micro-organisms with intracellular growth (Listeria, mycobacteria, corynobacteria . . . ).

The applications indicated previously by way of examples are not exclusive of other applicatio bringing into action the immunoregulator properties of the compounds according to the invention. There can also be cited by way of example, their reinforcing action at the level of this specific immunization of the host with regard to parasitic antigens, the restoration of the immunocompetence of the host, when the latter is at a lower level than normal, notably when the latter has been damaged by the antigens or parasites themselves, or under the effect of chemotherapy, radiotherapy, or any other treatment having an immunosuppressive action.

The pharmaceutical compositions according to the invention, generally, are useful for the treatment or the prevention of infectious diseases of bacterial or parasitic origin, or for the inhibition of tumoral diseases.

The adjuvants according to the invention can be administered to the host—animal or human being—in any suitable manner for producing the desired effect. Administraction of the immunoregulator principle, notably adjuvant, and of the immunogen agent, notably vaccinating antigen, can be contemplated simultaneously or separately, in the latter case if necessary staggered in time, if necessary again by similar or different routes of administration (for example parenteral and oral routes respectively or vice versa).

The invention relates naturally also to the various pharmaceutical compositions with which the compounds according to the invention can be incorporated, if necessary in association with other active substances. In particular, the compounds I are advantageously associated with immunogen agents, where, for example, immunogenic agents used at very low doses, or weak immunogenic agents, are concerned.

Advantageous pharmaceutical compositions are constituted by injectable solutions or suspensions containing an effective dose of at least one product according to the invention. Preferably, these solutions or suspensions are formed in an isotonic sterilized aqueous phase, preferably again saline or glucosed.

The invention relates more particularly to such suspensions or solutions which are suitable for administration by intradermal, intramuscular, or sub-cutaneous injection, or again by sacharification.

It relates also to pharmaceutical compositions administerable by other routes, notably by the oral or rectal route, or again in the form of aerosols designed to be applied to the mucous membranes, notably the ocular, nasal, pulmonary or vaginal mucous membranes.

In consequence, it relates to pharmaceutical compositions in which one at least of the compounds according to the invention is associated with pharmaceutically acceptable excipients, solid or liquid, adapted to the constitution of oral, ocular or nasal forms, or with excipients adapted for the constitution of rectal forms of administration, or again with gelatinous excipients for vaginal administration. It relates also to isotonic liquid compositions containing one at least of the products according to the invention, adapted for administration to the mucous membranes, notably the ocular or nasal mucous membranes.

It relates lastly to compositions formed of pharmaceutically acceptable liquified gases, of the "propellant" type, in which the products according to the invention are dissolved or held in suspension, and of which the release causes the dispersion in an aerosol.

The invention consists also of a method of treatment aimed at reinforcing the immunitary defenses of the host, consisting of administering to said host an effective dose of one at least of the products according to the invention, in one of the administerable forms which have been mentioned above. By way of example of doses capable of inducing an effect, may be mentioned doses of 10 to 1,000 µg per kg of body weight, for example of 50 µm, when the administration is effected by the parenteral route, or again of a dose of 200 to 20,000 µg per kg body weight, for example of 1,000 µg, for other methods of administration, such as for example the oral route.

Other characteristics of the invention will appear in the course of the description which follows of examples of the preparation of the products according to the invention, as well as of the tests establishing the pharmacological properties of these products.

Preparation of the oligomer of β-D-p.aminophenyl-glycoside MDP 100 mg of β-D-p.aminophenyl-glycoside of Mur-NAc-L-Ala-D-isoGln are dissolved in 10 ml of 0.2M sodium acetate at pH 4.0, and 0.2 cm$^3$ of 25% glutaraldehyde solution is added.

The mixture is left at room temperature (25° C.) for 16 hours, and 0.035 cm$^3$ of a solution of NaHSO$_3$ is added to neutralize the remaining carbonyl groups.

The reaction mixture is filtered on a column of SEPHADEX G.25 gel (2.5×200 cm) equilibrated in a pyridine acetate medium at pH 5.3, and eluted by the same medium.

The fractions corresponding to the compounds of higher molecular weights are the first eluted. They correspond approximately to the elution interval comprised between 375 ml and 426 ml. Fractions of lower molecular weight are eluted to about 600 ml. The fractions of highest molecular weight are combined and freeze-dried, then again subjected to passage over gel under the same conditions.

These fractions are again purified on a column of dimethylacrylate-polyethylene-glycol(FRACTOGEL PGM 2000). The product recovered is designated as being the polymer of β-D-p.aminophenyl-glycoside of Mur-NAc-L-Ala-D-isoGln (pol PAP-MDP).

The cross-linking of the PAP-MDP by the glutaraldehyde is followed qualitatively by thin layer chromatography on silica gel plates in a butanol/acetic acid/water (4/1/5) mixture. Equivalent samples of PAP-MDP and of the cross-linked product (25–50 µg in 1 to 2 µl of water) are subjected to chromatography, then dyed with ninydrin. The polymerized form does not show any visible stain, contrary to what is observed with the monomeric form PAP-MDP.

The UV diagrams of the monomer and of the polymer are also different. A single and well-defined peak is observed at 253 nm corresponding to the cross-linked product (pol PAP-MDP).

A first evaluation test of the molecular weight has been carried out by filtration on SEPHADEX G.100 gel showing a molecular weight of about 6000. As the controls used were polypeptide and non-glycopeptide in nature like MDP, and considering that the cross-linked fraction also has a relative elution volume (Ve/Vo) very close to that of the lowest molecular weight control (constituted by a bovine trypsin inhibitor whose molecular weight is 6513), the value of the determination must be considered as a reasonable order of magnitude.

The product obtained contained from 8 to 10 monomer units.

Preparation of
N$^\alpha$-N-acetyl-muramyl-L-alanyl-D-isoglutamine-N$^\epsilon$[N$^\alpha$-N-acetyl-muramyl-L-alanyl-D-isoglutamine-N$^\epsilon$(N$^\alpha$-N-acetyl-muramyl-L-alanyl-D-isoglutamine-lysyl)lysyl]-lysyl-amide, in abridged formula N$^\alpha$MDP-N$^\epsilon$[N$^\alpha$MDP-N$^\epsilon$(MDP-Lys)Lys]-Lys-NH$_2$, or again H(MDP-Lys)$_3$-NH$_2$ The abbreviations used in the description below have the following significances:

| | |
|---|---|
| BOC | t-butyloxycarbonyl |
| Z | benzyloxycarbonyl |
| OSu | hydroxy-succinimidic ester |
| Lys | lysine |
| Lys-NH$_2$ | lysine amide |
| MDP | N—acetyl-muramyl-L-alanyl-D-isoglutamine |

N$^\alpha$BOC-N$^\epsilon$Z-Lys-NH$_2$ (A)

2.38 g (5 mmoles) of N$^\alpha$BOC-N$^\epsilon$Z-Lys-OSu, obtained in the manner described by P. Hartter in Z. Physiol. Chem. (1976) 357, 1683, dissolved in 100 ml of ethyl acetate, are treated by a current of dry ammonia for 1 hour at ambient temperature. The organic solution is then washed with water until neutral pH, then dried over MgSO$_4$, and concentrated. The product is precipitated in ethyl acetate-ether. 1.63 g of product as obtained whose characteristics are: MP 140°–141° C.; $[\alpha]_D^{25} = +1.5°$ (absolute methanol).

Elementary analysis of this product is:

| for C$_{19}$H$_{29}$N$_3$O$_5$ (379.46) | C | H | N |
|---|---|---|---|
| calculated | 60.14 | 7.70 | 11.07 |
| found | 59.86 | 7.70 | 10.73 |

N$^\alpha$BOC-N$^\epsilon$(N$^\alpha$BOC-N$^\epsilon$Z-Lys)-Lys-NH$_2$

(B)

759 mg (2 mmoles) of (A), dissolved in 25 ml of glacial acetic acid, are hydrogenated for 4 hours in the presence of 5% palladium on charcoal. After filtration of the catalyst, the solution is concentrated to dryness and the residue obtained is dried under vacuum in the presence of KOH. It is taken up again in 5 ml of dimethylformamide containing 0.21 ml of N-methylmorpholine. 716 mg (1.5 mmoles) of N$^\alpha$BOC-N$^\epsilon$Z-Lys-OSu are then added to this solution. The reaction mixture is left for 20 hours at ambient temperature, then concentrated to dryness. The residue is taken up again in 100 ml of ethyl acetate, and washed successively with a solution of 10% citric acid, in water, with a molar solution of NaHCO$_3$, and in water at a neutral pH. The organic phase is dried over MgSO$_4$, filtered, then concentrated. By precipitation with ether, 652 mg of product are recovered whose characteristics are: M.P. 77°–79° C.; $[\alpha]_D^{25} = -6.7°$ (glacial acetic acid).

The elementary analysis of this product is:

| for C$_{30}$H$_{49}$N$_5$O$_8$ (607.76) | C | H | N |
|---|---|---|---|
| calculated | 59.29 | 8.13 | 11.52 |
| found | 59.43 | 8.17 | 11.55 |

N$^\alpha$BOC-N$^\epsilon$[N$^\alpha$BOC-N$^\epsilon$(N$^\alpha$BOC-N$^\epsilon$Z-Lys)-Lys]-Lys-NH$_2$

(C)

1.2 g (2 mmoles) of (B) are hydrogenated, then coupled with 716 mg (1.5 mmoles) of N$^\alpha$BOC-N$^\epsilon$Z-Lys-OSu essentially according to the experimental method described for (B). 1.14 g of product whose characteristics are: M.P. 94°–98° C.; $[\alpha]_D^{25} = -9.4°$ (absolute methanol), are obtained.

The elementary analysis of this product is:

| for C$_{41}$H$_{69}$N$_7$O$_{11}$ (836.05) | C | H | N |
|---|---|---|---|
| calculated | 58.90 | 8.32 | 17.73 |
| found | 59.07 | 8.38 | 11.39 |

The derivative (C) is debutyloxycarboxylated in the usual way by the action of a solution of normal HCl in acetic acid for 30 minutes. The reaction mixture was concentrated to dryness and the product was obtained by precipitation with ether (C').

N$^\alpha$MDP-N$^\epsilon$[N$^\alpha$MDP-N$^\epsilon$(MDP-Lys)-Lys]-Lys-NH$_2$

(D)

108.4 mg (0.22 mmole) of MDP, obtained in the manner described by P. LEFRANCIER, J. CHOAY, M. DERRIEN and I. LEDERMAN in Int. J. Peptide Protein Res. (1977) 9,249, were dissolved in 2.5 ml of dimethylformamide. After the addition of 31 mg of N-hydroxybenzotriazole and of 45 mg of dicyclohexylcarbodiimide, the reaction mixture was left for 1 hour at ambient temperature. 21.5 mg (0.333 mmole) of (C'), dissolved in 2.5 ml of dimethylformamide containing 11 μl of N-methylmorpholine, were then added. After one night, the reaction mixture is concentrated to dryness. The residue is taken up again in water and the dicyclohexylurea is removed by filtration. By lyophilization of the filtrate, 130 mg of product is obtained. It is dissolved in a mixture of $2.10^{-3}$M acetic acid and of dimethylformamide (3/1) and eluted in this same mixture from a column of AGIX 2 (1×10 cm). The interesting fractions are combined, concentrated and taken up in a mixture of 0.1M acetic acid and dimethylformamide (3/1). The product is eluted in this same mixture from a column (1×10 cm) of AG 50 WX 2. The interesting fractions are combined, concentrated, and taken up in 10 ml of a mixture of methanol and water (50/50) containing 0.5 ml of acetic acid. The product is hydrogenated for 4 hours in the presence of 5% palladium on charcoal. The catalyst is removed by filtration. The product is obtained, after concentration of the filtrate, by freeze-drying (50 mg).

41 mg of this crude product were finally purified by means of a column of BIOREX 70 (10×1 cm), by successive elutions with solutions of $2.10^{-3}$M and 1M of acetic acid.

The interesting fractions were combined and freeze-dried. 25 mg of product was obtained with rotatory power $[\alpha]_D^{25} = +22.5°$ (glacial acetic acid).

The amino acid analysis of a total acid hydrolysate (HCl 6N, 100° C., 24 hours) gives the theoretical values: Ala: 0.99 (1)—Glu: 1.02 (1)—Lys: 0.99 (1).

Preparation of N$^\epsilon$.N$^{\epsilon''}$bis(N-acetyl-muramyl-L-alanyl-D-isoglutamine-L-lysine)-adipimidyl, dichlorohydrate or briefly adipimidyl-bis(MDP-Lys)

124 mg (0.2 mmole) of N-acetyl-muramyl-L-alanyl-D-isoglutamine-L-lysine, acetate were dissolved in 20 ml of a mixture of dimethylformamide and of pyridine (50/50) containing 22 μl of N-methylmorpholine. To this solution, 49 mg (0.2 mmole) of dimethyladipimidate, dihydrochloride and 45 μl of N-methylmorpholine were added. After 20 hours, at room temprature, 24.5 mg (0.1 mmole) of dimethyladipimidate, dihydrochloride and 22 μl of N-methylmorpholine were again added. The reaction was allowed to continue for a further 24 hours, then the reaction mixture was concentrated to dryness. By precipitation in a mixture of dimethylformamide-ether, 210 mg of product were obtained. This crude product was taken up again in 1 ml of dimethylformamide and loaded onto a column of LH-20 (80×2.5 cm) eluted with dimethylformamide. The interesting fractions were combined, concentrated almost to dryness, and the product was precipitated with ether (107 mg). This product, partially purified, was dissolved in 0.5 ml of an ethyl acetate-pyridine-acetic acid-water mixture (5/5/1/2) and 0.1 ml of water, then charged onto a silica column (MERCK, type A) previously equilibrated and eluted with the preceding mixture. The interesting fractions were collected, concentrated and repurified in the same manner a second time. By freeze-drying, 40 mg of product were finally collected.

Elementary analysis of this product is:

| for $C_{56}H_{98}N_{14}O_{24}Cl_2$, 2 $H_2O$ | C | H | N |
|---|---|---|---|
| calculated | 46.11 | 6.99 | 13.44 |
| found | 46.19 | 7.076 | 13.37 |

PHARMACOLOGICAL PROPERTIES (1) Toxicity

The toxicity of the products according to the invention were studied by parenteral administration in mice. It was observed that the toxic doses were of an order of magnitude very much higher than that of the doses at which these products manifest their activity.

Thus, the tests by injection by the intravenous route in the suprarenalectomized mouse, whose sensitivity to endotoxins is well known, showed that the lethal dose 50 for the pol (PAP-MDP) is higher than 100 $\mu$g, whilst, for the endotoxin extracted from *E. coli*, it is only 0.2 $\mu$g. The product is hence 5000 times less toxic by this test. In addition, the activity/toxicity ratio is very favorable in the case of the pol-PAP-MDP, as appears when one considers the results of the tests reported below.

(2) Limulus Test

To show the absence of activity of the endotoxic type, products according to the invention were subjected to the Limulus test. For this purpose, 0.1 ml of the Limulus amoebocyte lysate preparation (marketed by the MALLINCKRODT Company, at Saint Louis, U.S.A.) was mixed with an equal volume of the tested product at various concentrations in solution in apyrogenic distilled water. The vessels used were also made apyrogenic by dry heating in the oven, at 180° C., for 2 hours.

After incubating the mixture for 20 minutes at 37° C. in tubes, the formation of gel characteristic of the presence of endotoxin was estimated.

A test is positive when the presence of a firm gel is observed which remains adherent to the bottom of the tube when the latter is inverted (technique described by Elin R. J. and Wolff S. M., J. Infect. Dis., 1973, 126: 349).

In the case of the pol (PAP-MDP), the concentration leading to a positive response is of the order of 15 $\mu$g/ml. Under the same conditions, the LPS extract of *Escherichia coli* by way of comparison is positive at 0.03 ng/ml. It is hence observed that the pol (PAP-MDP) is 500,000 times less active than the LPS on this test. Considering the respective active doses 10 $\mu$g and 0.01 $\mu$g per mouse (see the results reported in the following tests), the anti-infectious activity cannot be due to contamination by endotoxins.

(3) Adjuvant character in the aqueous phase and in emulsion (a) In the aqueous phase Groups of 8 Swiss mice aged two months received, by sub-cutaneous injection (SC), 0.5 mg of antigen constituted by bovine serum albumin (BSA) with 0.1 mg or without the tested substance in an isotonic saline solution. This high dose of antigen, because it is situated at the limit of the paralyzing dose with respect to the immunitary response, results, for this reason, in a weak or zero response to the antigen only in the controls: It constitutes therefore a severe criterion to establish the activity of an adjuvant substance. Thirty days later, the mice received, by the same administrative route, a booster containing 0.1 mg of the same antigen.

The antibody level was determined, six days after the booster, by passive hemagglutination using sheep's red blood corpuscles treated with formalin and covered with the antigen studied according to the method described by A. A. HIRATA and M. W. BRANDISS (J. Immunol., 100, 641-648, 1968).

The antibody titer, represented by the maximum serum dilution agglutinating a given amount of sheep corpuscles, reaches a maximum at the 36th day. The results obtained for various products according to the invention are shown in Table I. By way of comparison, the results obtained with MDP are indicated, on the one hand, and for PAP-MDP, on the other hand.

TABLE 1

| Adjuvant activity of the products administered in an isotonic saline solution | | |
|---|---|---|
| Adjuvant in saline solution | Dose $\mu$g | Antibody titer |
| Controls | | 6 |
| MDP | 100 | 200 |
| PAP-MDP | 100 | 11 |
| Pol (PAP-MDP) | 100 | 50 |
| (MDP)$_2$ L-Lys OMe | 100 | 200 |
| H(N—$\alpha$-MDP-Lys)$_3$ NH$_2$ | 100 | 200 |
| Adipimidyl-bis-MDP-Lys | 100 | 200 |

(b) In emulsion

The tests were carried out on batches of 6 male Hartley guinea pigs of 350 g. The administration was done by intradermal injection into the plantar pad of each of the rear paws. Ovalbumin (constituting the antigen) in the amount of 1 mg is prepared in 0.1 ml of an emulsion of saline isotonic solution, in an oily phase constituted either by the Freund incomplete adjuvant (FIA) or by the complete adjuvant (FCA) formed by the FIA to which is added 0.1 mg of whole *Mycobacterium smegmatis* cells. The compound according to the invention was administered in the amount of 0.05 mg added in the emulsion containing the FIA.

Eighteen days after this immunization, possible delayed hypersensitivity reactions to the antigen were sought by injecting by the intradermal route 0.01 mg of ovalbumin in the side of the animals, and 48 hours later, the reaction of the point of injection was observed. The diameter in millimeters of the reaction thus-caused was measured.

Twenty-one days after the injection, the animals were bled. On the collected serum, the content of specific antibodies of the ovalbumin was measured by precipitation of the antibody-antigen complex in the equivalence zone. The amount of protein nitrogen contained in the precipitate was estimated by the Folin method. The average values of the contents of the antibodies are indicated in the Table 2. These values express the amount, in micrograms, of nitrogen precipitatable by the antigen, per milliliter of the serum.

The results of these tests are as follows.

TABLE 2

| Composition of the emulsion containing the antigen | Serum antibodies (μg/ml) | Cutaneous test diameter in mm |
|---|---|---|
| FIA | 500 | 0 |
| FCA (FIA + mycobacteria 50 μg) | 1500 | 10 |
| FIA + MDP (50 μg) | 3240 | 11.3 |
| FIA + PAP-MDP (50 μg) | 3480 | 14.4 |
| FIA + (MDP)$_2$ L-Lys OMe (50 μg) | 5000 | 17 |
| FIA + (H(N—α-MDP-Lys)$_3$NH$_2$ | 5500 | 16 |
| FIA + adipimidyl-bis-MDP-Lys | 6000 | 17 |

These results show that the tested products caused, a considerable increase in the level of the antibodies formed.

The administration of the product also generates a delayed type of hypersensitization in the treated subject with respect to the antigen, which hypersensitization is revealed by the cutaneous test.

(4) Anti-infectious activity with respect to Klebsiella

The testing procedure is described in the article CHEDID L. et coll., Proc. Natl. Acad. Sci. USA, 74:2089.

In this way there was previously established an experimental method permitting the anti-infectious character of the product to be demonstrated. It was shown that a dose of about $10^4$ *Klebsiella pneumoniae*, injected by the intramuscular route in mice, results in the gradual death of a considerable part, if not all, of the animals in the week following the inoculation. After 8 days, the survival of the animals was definitely achieved.

The survival of groups of inoculated mice under the above conditions and treated by means of the products according to the invention was followed.

For these tests, hybrid mice (C57B1/6×AKR) FI bred at the PASTEUR INSTITUTE, from strains derived from the CNRS breeding station at ORLEANS, were used.

The infection by *Klebsiella pneumoniae*, a strain of the capsular 2, biotype d type, was done from a culture of 16 hours in a medium for pneumococci (No. 53515, PASTEUR INSTITUTE).

Various treatment conditions and tests have been studied. Thus, the treatment was carried out either 24 hours before the test, or 1 hour after the latter. The influence of the infecting dose and the mode of administration has also been studied. In particular, the protective properties of the products have been determined in the case of an injection of *Klebsiella pneumoniae* by the intravenous route, which corresponds to a severe infection.

In the majority of cases, the tests have been carried out on mice aged from 5 to 6 weeks. In one part of the tests, on the other hand, mice 7 days old were used, since the immune responses, in very young subjects are substantially different, and, on the whole, much more difficult to stimulate than those that are observed in adult subjects. It hence was interesting to observe the activity of the products in both cases.

The products are administered in apyrogenic physiological solution in the proportion of 0.2 ml for intravenous administration to adult mice and 0.05 ml for subcutaneous injection to mice 7 days old. The controls received the solution alone.

The conditions and results of these tests are reported in the following Tables 3 and 4. The percentage protection indicated corresponds to the difference in percentages of survivors of the treated group with respect to the control group.

By way of comparison, there are shown the results of tests obtained with MDP and with paraminophenylglycoside MDP.

The results expressed in these tables represent several identical experiments and these data are shown to be reproducible.

TABLE 3

Anti-*klebsiella Pneumoniae* activity in the adult mouse

| K. pneumoniae infection Admin-ist. | Dose | Time | Product | Mode | Dose μg | D0 | D + 3 | D + 5 | D + 10 | % Protection |
|---|---|---|---|---|---|---|---|---|---|---|
| i.m. | 1.5 × 10$^4$ | −24 h | (Controls) | i.v. | — | 32 | 14 | 10 | 4 | |
| | | | MDP | " | 100 | 32 | 32 | 32 | 20 | 50 |
| " | " | " | (Controls) | " | — | 32 | 16 | 10 | 3 | |
| | | | PAP-MDP | " | 100 | 40 | 28 | 17 | 11 | 19 |
| " | " | " | (Controls) | " | — | 24 | 15 | 9 | 5 | |
| | | | Pol(PAP-MDP) | " | 10 | 24 | 24 | 21 | 19 | 58 |
| | | | " | " | 100 | 24 | 24 | 24 | 22 | 72 |
| " | " | " | (Controls) | " | — | 24 | 15 | 11 | 3 | |
| | | | (MDP)$_2$-L-Lys-OME | " | 100 | 24 | 22 | 18 | 13 | 41 |
| " | " | " | (Controls) | " | — | 24 | 7 | 1 | 1 | |
| | | | H(MDP-Lys)$_3$NH$_2$ | " | 100 | 24 | 20 | 17 | 15 | 58 |
| " | " | " | (Controls) | " | — | 32 | 13 | 9 | 8 | |
| | | | Adipimydil-bis-MDP-Lys | " | 100 | 32 | 27 | 23 | 22 | 44 |
| i.m. | 1.5 × 10$^4$ | +1 h | (Controls) | i.v. | — | 24 | 12 | 6 | 1 | |
| | | | MDP | " | 100 | 24 | 20 | 16 | 11 | 42 |
| " | " | " | (Controls) | " | — | 16 | 13 | 8 | 3 | |
| | | | Pol(PAP-MDP) | " | 10 | 16 | 16 | 13 | 11 | 50 |
| | | | " | " | 100 | 16 | 16 | 16 | 16 | 81 |
| i.v. | 1.5 × 10$^3$ | −24 h | (Controls) | i.v. | — | 32 | 11 | 8 | 4 | |
| | | | MDP | " | 100 | 16 | 14 | 11 | 9 | 44 |
| | | | PAP-MDP | " | 100 | 24 | 6 | 2 | 2 | 0 |
| | | | Pol(PAP-MDP) | " | 10 | 32 | 22 | 17 | 9 | 16 |
| | | | " | " | 100 | 16 | 15 | 14 | 14 | 75 |
| i.v. | 1.5 × 10$^5$ | −24 h | (Controls) | i.v. | — | 24 | 0 | 0 | 0 | |
| | | | MDP | " | 100 | 24 | 2 | 0 | 0 | |

TABLE 3-continued

| K. pneumoniae infection | | | Treatment | | Dose | Number of mice | | | | % Protection |
|---|---|---|---|---|---|---|---|---|---|---|
| Admin-ist. | Dose | Time | Product | Mode | μg | D0 | D + 3 | D + 5 | D + 10 | |
| | | | Pol(PAP-MDP) | " | 100 | 24 | 12 | 4 | 3 | 12 |

The results obtained show that the products according to the invention, in varying degrees, have notable anti-infectious activity with respect to infections caused by the inoculation of *Klebsiella pneumoniae*. This activity is manifested, whether the product is administered before or even at the same time as the infecting injection (or even shortly after the latter). This activity is appreciable even for the most severe conditions of infection, that is to say those for which the inoculation is conducted by the intravenous route and, in particular, for high doses of infecting injections.

It must also be noted that, surprisingly, the oligomer of p.aminophenyl-glycoside MDP obtained by coupling to glutaraldehyde is anti-infectious, whereas the p-aminophenyl-glycoside MDP alone is practically not.

The results reported in the following table represent the tests carried out in mice aged 7 days.

TABLE 4

Anti-*Klebsiella-pneumoniae* activity in the 7 day old mouse

| | | | | | | | | | | |
|---|---|---|---|---|---|---|---|---|---|---|
| s.c. | $10^3$ | −24 | (Controls) | s.c. | — | 53 | 20 | 14 | 11 | |
| " | " | " | MDP | " | 100 | 48 | 37 | 26 | 22 | 25 |
| | | | LPS | " | 0.01 | 38 | 9 | 3 | 3 | |
| " | " | " | (Controls) | " | — | 28 | 15 | 13 | 10 | |
| " | " | " | Pol(PAP-MDP) | " | 100 | 27 | 22 | 19 | 19 | 34 |
| i.v. | $2.5 \times 10^2$ | −24 h | (Controls) | s.c. | — | 28 | 0 | | | |
| " | " | " | MDP | " | 100 | 28 | 7 | 5 | 5 | 18 |
| " | " | " | (Controls) | " | — | 21 | 0 | | | |
| " | " | " | Pol(PAP-MDP) | " | 100 | 22 | 14 | 10 | 9 | 41 |

The results obtained show that the oligomer of p.aminophenyl-glucoside MDP obtained by coupling to glutaraldehyde has notable anti-infectious activity. This activity is remarkable in the animals of which it is known that the immune responses are very low at this age and which cannot be protected by LPS under the conditions of the experiment.

(5) Anti-infectious activity with respect to Listeria

Under similar conditions to those of the tests of (4), the influence of the administration of the oligomer of p.aminophenyl-glycoside MDP was determined on the mortality of mice in which a dose of *Listeria monocytogenes* is administered, known for generating typically an infection of cellular type. As previously, the action of the product according to the invention was compared with that of *Corynebacterium granulosum* of which the anti-infectious properties are well known in this field. It was also determined, still by way of comparison, the action of Mur-NAc-L-Ala-D-isoGln (MDP).

The treatment of the mice and the inoculation were carried out intravenously. The injected products were in solution or suspension in 0.2 ml of apyrogenic physiological solution. The controls only received the solution.

The dose of Listeria administered was, in all the tests, $1.10^3$ units.

The test whose results are given below have been carried out varying the doses of the tested products and the interval of time separating the treatment of inoculation of the *Listeria monocytogenes* (either 1, or 7 days). The number of surviving mice at the fifth and the tenth day following the inoculation was followed, and the percentage protection determined as for the preceding tests.

TABLE 5

Anti-*Listeria monocytogenes* activity in the adult mouse

| Listeria Infection | | | Treatment | | Dose | Number of mice | | | % Protection |
|---|---|---|---|---|---|---|---|---|---|
| Admin-ist. | Dose | Time | Product | Mode | μg | D0 | D + 5 | D + 10 | |
| i.v. | $10^3$ | — | (Controls) | i.v. | — | 24 | 3 | 2 | |
| | | D-1 | Corynebacterium | " | 300 | 8 | 0 | 0 | |
| | | D-7 | " | " | 300 | 24 | 12 | 11 | 38 |
| " | " | — | (Controls) | " | — | 40 | 9 | 4 | |
| | | D-1 | MDP | " | 100 | 32 | 6 | 2 | 0 |
| " | " | — | (Controls) | " | — | 24 | 11 | 2 | |
| | | D-1 | Pol(PAP-MDP) | " | 10 | 16 | 10 | 6 | 29 |
| | " | " | | " | 100 | 24 | 23 | 19 | 71 |

These results show, on the one hand, the absence of protection in practice by means of MDP under the experimental conditions and, on the other hand, a very significant protection in the case of the product according to the invention since it is manifested more rapidly than in the case of Corynebacterium used as reference product.

We claim:

1. A water soluble oligomer free of N-acetyl-glucosamine units which oligomer is a non-specific immunospecific immunostimulant which is virtually non-immunogenic and comprises at least two to ten muramyl peptide monomer units linked to each other directly or through a coupling group, said monomer units having the formula

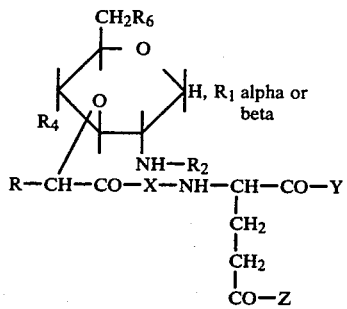

in which

R is hydrogen or methyl,
$R_1$ is $-HN_2$, $-OH$, aminoethoxy para-aminophenyloxy or glutaraldehyde,
$R_2$ is hydrogen or acetyl,
$R_4$ is hydroxyl, $R_6$ is $-NH_2$, $-OH$, acetyl or succinyl,
X is L-alanyl, L-seryl, L-threonyl, L-prolyl, L-valyl or glycyl,
Y is $-OH$, methoxy, ethoxy or proproxy, and Z being a linking group which links the mimmer units and which comprises hydroxyl, amino, or lysyl.

2. A water soluble oligomer free of N-acetyl glucosamine units which comprises two Mur-N-Ac-L-Ala-D-isoGln units or the nor-Mur homologue linked to each other by a lysine residue, optionally amidated or esterified and having the formula:

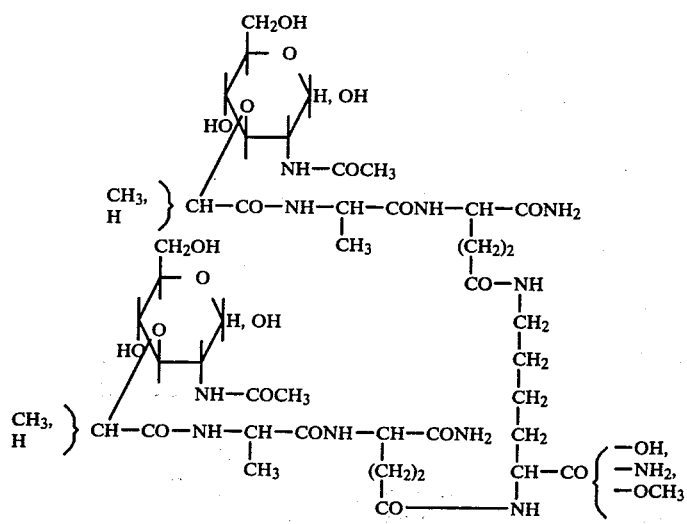

3. A water soluble oligomer free of N-acetylglucosamine which comprises three units of Mur-N-Ac-L-Ala-D-isoGln units or the nor-Mur homologue linked to a peptide chain which comprises three lysine links, the terminal carboxyl of the chain optionally being amidated or esterified, and having the formula

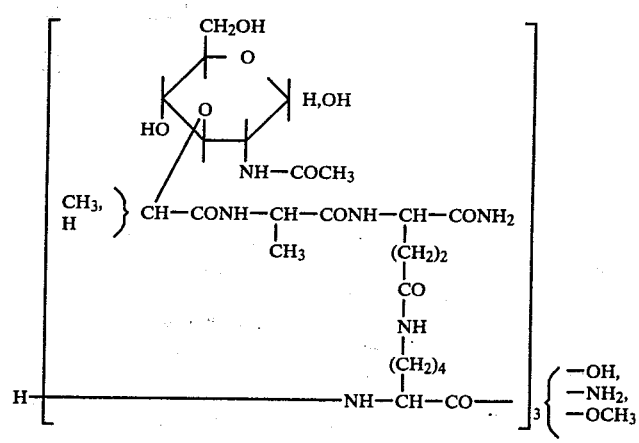

4. A water soluble oligomer free of N-acetylglucosamine units which comprises two units of Mur-N-Ac-L-Ala-D-iso-Gln-L-Lys or the nor-Mur homologue linked to each other by adipimidine or a homologue thereof and having the formula

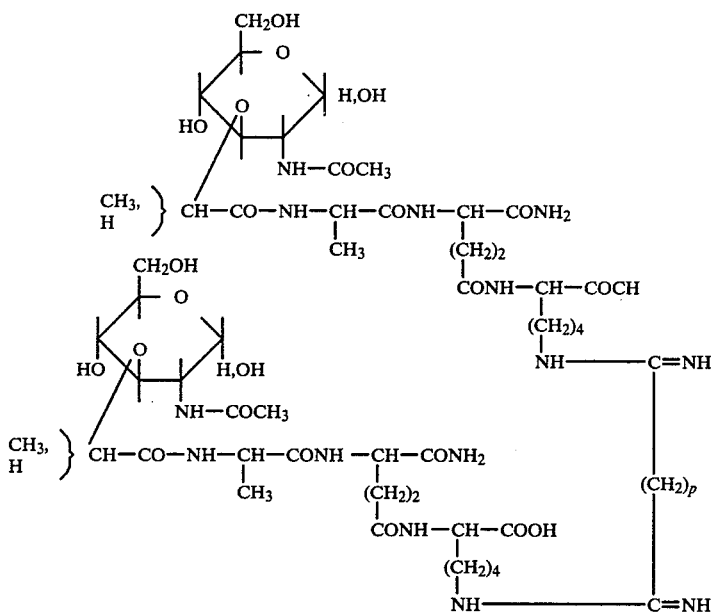

in which p is from 2 to 10.

5. The oligomer of claim 1 wherein the monomer is selected from the group consisting of:

N-acetyl-muramyl-L-alanyl-D-isoglutamine and the methyl, ethyl and propyl ester;

N-acetyl-muramyl-L-alanyl-D-glutamic acid, its diamide, its alpha-ester, and methyl, ethyl, propyl diester;

N-acetyl-muramyl-L-alanyl-D-glutamine and its methyl, ethyl, propyl ester;

N-acetyl-muramyl-L-seryl-D-isoglutamine, the alpha-glycidyl amide of N-acetyl-muramyl-L-alanyl-D-glutamic acid;

N-acetyl-muramyl-L-alanyl-D-isoglutaminyl-L-lysine and its methyl and ethyl ester;

N-acetyl-muramyl-L-alanyl-D-isoglutaminyl-L-alanine;

N-acetyl-muramyl-L-alanyl-D-isoglutaminyl-L-lysyl-L-alanine;

4,6-di-O-acetyl-N-acetyl-muramyl-L-alanyl-D-isoglutamine;

6-O-succinyl-N-acetyl-muramyl-L-alanyl-D-isoglutamine;

the methyl ester of 4,6-di-O-succinyl-N-acetyl-muramyl-L-alanyl-D-isoglutamine; and the methyl-ester of 4-O-acetyl-6-O-(N-alpha-lysylamide)-succinyl-N-acetyl-muramyl-L-alanyl-D-isoglutamine.

6. A biological composition which comprises a biologically acceptable diluent and an oligomer of claims 1, 2, 3, 4 or 5.

7. The therapeutic method which comprises administering to a host a composition which comprises a biologically acceptable diluent and an oligomer of claims 1, 2, 3, 4 or 5.

* * * * *